US010023639B2

(12) United States Patent
Li et al.

(10) Patent No.: US 10,023,639 B2
(45) Date of Patent: Jul. 17, 2018

(54) MULTI-FUNCTIONAL ANTIBODY POLYPEPTIDE FOR CRYPTIC EPITOPE OF EPIDERMAL GROWTH FACTOR RECEPTOR AND T CELL ANTIGEN

(71) Applicant: CARSGEN THERAPEUTICS CO., LTD., Shanghai (CN)

(72) Inventors: Zonghai Li, Shanghai (CN); Hua Jiang, Shanghai (CN); Bizhi Shi, Shanghai (CN); Huamao Wang, Shanghai (CN); Juan Kong, Shanghai (CN); Huiping Gao, Shanghai (CN)

(73) Assignee: CARSGEN THERAPEUTICS CO., LTD., Shanghai (CN)

( * ) Notice: Subject to any disclaimer, the term of this patent is extended or adjusted under 35 U.S.C. 154(b) by 320 days.

(21) Appl. No.: 14/389,665

(22) PCT Filed: Mar. 4, 2013

(86) PCT No.: PCT/CN2013/072098
§ 371 (c)(1),
(2) Date: Sep. 30, 2014

(87) PCT Pub. No.: WO2013/149526
PCT Pub. Date: Oct. 10, 2013

(65) Prior Publication Data
US 2015/0093386 A1  Apr. 2, 2015

(30) Foreign Application Priority Data
Apr. 1, 2012 (CN) .......................... 2012 1 0094008

(51) Int. Cl.
C07K 16/28 (2006.01)
C07K 14/71 (2006.01)
A61K 39/00 (2006.01)

(52) U.S. Cl.
CPC .......... *C07K 16/2863* (2013.01); *C07K 14/71* (2013.01); *C07K 16/2809* (2013.01); *A61K 2039/505* (2013.01); *C07K 2317/24* (2013.01); *C07K 2317/31* (2013.01); *C07K 2317/34* (2013.01); *C07K 2317/622* (2013.01); *C07K 2317/73* (2013.01)

(58) Field of Classification Search
None
See application file for complete search history.

(56) References Cited

U.S. PATENT DOCUMENTS

| | | |
|---|---|---|
| 7,112,324 B1 | 9/2006 | Dorken et al. |
| 2008/0176247 A1 | 7/2008 | Chou et al. |
| 2011/0076232 A1 | 3/2011 | Old et al. |
| 2012/0189630 A1 | 7/2012 | Bigner et al. |

FOREIGN PATENT DOCUMENTS

| | | |
|---|---|---|
| CN | 101602808 A | 12/2009 |
| CN | 101687915 A | 3/2010 |
| CN | 102405235 A | 4/2012 |
| EP | 0 239 400 A2 | 9/1987 |
| WO | WO 89/09622 A1 | 10/1989 |
| WO | WO 90/07861 A1 | 7/1990 |
| WO | WO 91/10741 A1 | 7/1991 |
| WO | WO 94/02602 A1 | 2/1994 |
| WO | WO 2005/010151 A2 | 2/2005 |
| WO | WO 2008/119567 A2 | 10/2008 |
| WO | WO 2009/023265 A1 | 2/2009 |
| WO | 2010/096434 A2 | 8/2010 |
| WO | WO 2010/096434 A2 | 8/2010 |
| WO | WO 2010/127284 A2 | 11/2010 |
| WO | WO 2011/035465 A1 | 3/2011 |

OTHER PUBLICATIONS

Paul, W.E. Fundamental Immunology, 3rd Edition, 1993, pp. 292-295.*
MacCallum R.M. et al, Antibody-antigen interactions: Contact analysis and binding site topography. J. Mol. Biol., 1998, vol. 262, p. 732-745.*
Casset F, et al. A peptide mimetic of an anti-CD4 monoclonal antibody by rational design. Biochemical and Biophysical Research Communications, 2003, vol. 307, p. 198-205.*
Bendig, M.M. Humanization of rodent monoclonal antibodies by CDR grafting. Methods: A Companion to Methods in Enzymology, 1995; vol. 8, p. 83-93.*
International Search Report and Written Opinion dated Jun. 13, 2013 for PCT/CN2013/072098.
International Preliminary Report on Patentability dated Oct. 9, 2014 for PCT/CN2013/072098.
Divgi et al., Phase I and imaging trial of indium 111-labeled anti-epidermal growth factor receptor monoclonal antibody 225 in patients with squamous cell lung carcinoma. J Natl Cancer Inst. Jan. 16, 1991;83(2):97-104.
Garrett et al., Antibodies specifically targeting a locally misfolded region of tumor associated EGFR. Proc Natl Acad Sci U S A. Mar. 31, 2009;106(13):5082-7. doi: 10.1073/pnas.0811559106. Epub Mar. 16, 2009.
Henion et al., Avian transitin expression mirrors glial cell fate restrictions during neural crest development. Dev Dyn. May 2000;218(1):150-9. PubMed PMID: 10822267.
Jiang et al., Growth suppression of human hepatocellular carcinoma xenografts by a monoclonal antibody CH12 directed to epidermal growth factor receptor variant III. J Biol Chem. Feb. 18, 2011;286(7):5913-20. doi: 10.1074/jbc.M110.192252. Epub Dec. 16, 2010.
Lutterbuese et al., T cell-engaging BiTE antibodies specific for EGFR potently eliminate KRAS- and BRAF-mutated colorectal (Continued)

*Primary Examiner* — Michael Pak
(74) *Attorney, Agent, or Firm* — Wolf, Greenfield & Sacks, P.C.

(57) ABSTRACT

Multi-functional antibody polypeptide comprises:
(a) a first functional domain, specifically recognizing a cryptic epitope formed by 287th to 302nd amino acid sequence of the EGFR, shown as SEQ ID NO:1, and
(b) a second functional domain, specifically recognizing the surface antigen of a human T cell.

8 Claims, 5 Drawing Sheets

(56) References Cited

OTHER PUBLICATIONS cancer cells. Proc Natl Acad Sci U S A. Jul. 13, 2010;107(28):12605-10. doi: 10.1073/pnas.1000976107. Epub Jun. 28, 2010.

Malmborg et al., BIAcore as a tool in antibody engineering. J Immunol Methods. Jun. 14, 1995;183(1):7-13.

Perera et al., Treatment of human tumor xenografts with monoclonal antibody 806 in combination with a prototypical epidermal growth factor receptor-specific antibody generates enhanced anti-tumor activity. Clin Cancer Res. Sep. 1, 2005;11(17):6390-9.

Pfosser et al., Role of target antigen in bispecific-antibody-mediated killing of human glioblastoma cells: a pre-clinical study. Int J Cancer. Feb. 9, 1999;80(4):612-6. PubMed PMID: 9935165.

Reusch et al., Anti-CD3 x anti-epidermal growth factor receptor (EGFR) bispecific antibody redirects T-cell cytolytic activity to EGFR-positive cancers in vitro and in an animal model. Clin Cancer Res. Jan. 1, 2006;12(1):183-90. PubMed PMID: 16397041.

Schier et al., Efficient in vitro affinity maturation of phage antibodies using BIAcore guided selections. Hum Antibodies Hybridomas. 1996;7(3):97-105.

Scott et al., A phase I clinical trial with monoclonal antibody ch806 targeting transitional state and mutant epidermal growth factor receptors. Proc Natl Acad Sci U S A. Mar. 6, 2007;104(10):4071-6. Epub Feb. 28, 2007. Erratum in: Proc Natl Acad Sci U S A. Oct. 2, 2007;104(40):15965. Ritter, Gerd [added].

Xu et al., Acquired resistance of lung adenocarcinoma to EGFR-tyrosine kinase inhibitors gefitinib and erlotinib. Cancer Biol Ther. Apr. 15, 2010;9(8):572-82. Epub Apr. 26, 2010.

Beare et al., Monoclonal antibodies to human cell surface antigens. Curr Protoc Immunol. Feb. 2008;Appendix 4:4A. doi: 10.1002/0471142735.ima04as80.

Extended European Search Report for EP 13772058.7, dated Sep. 30, 2015.

Asano et al., Cytotoxic enhancement of a bispecific diabody by format conversion to tandem single-chain variable fragment (taFv): the case of the hEx3 diabody. J Biol Chem. Jan. 21, 2011;286(3):1812-8. doi: 10.1074/jbc.M110.172957. Epub Nov. 19, 2010.

Knuth et al., Induction of tumour cell lysis by a bispecific antibody recognising epidermal growth factor receptor (EGFR) and CD3. Eur J Cancer. 1994;30A(8):1103-7.

Negri et al., In vitro and in vivo stability and anti-tumour efficacy of an anti-EGFR/anti-CD3 F(ab')2 bispecific monoclonal antibody. Br J Cancer. Oct. 1995;72(4):928-33.

Reusch et al., Anti-CD3 x anti-epidermal growth factor receptor (EGFR) bispecific antibody redirects T-cell cytolytic activity to EGFR-positive cancers in vitro and in an animal model. Clin Cancer Res. Jan. 1, 2006;12(1):183-90.

Scott et al., A phase I clinical trial with monoclonal antibody ch806 targeting transitional state and mutant epidermal growth factor receptors. Proc Natl Acad Sci U S A. Mar. 6, 2007;104(10):4071-6. Epub Feb. 28, 2007.

Ware et al., Tumor necrosis factor (TNF) receptor expression in T lymphocytes. Differential regulation of the type I TNF receptor during activation of resting and effector T cells. J Immunol. Dec. 15, 1991;147(12):4229-38.

\* cited by examiner

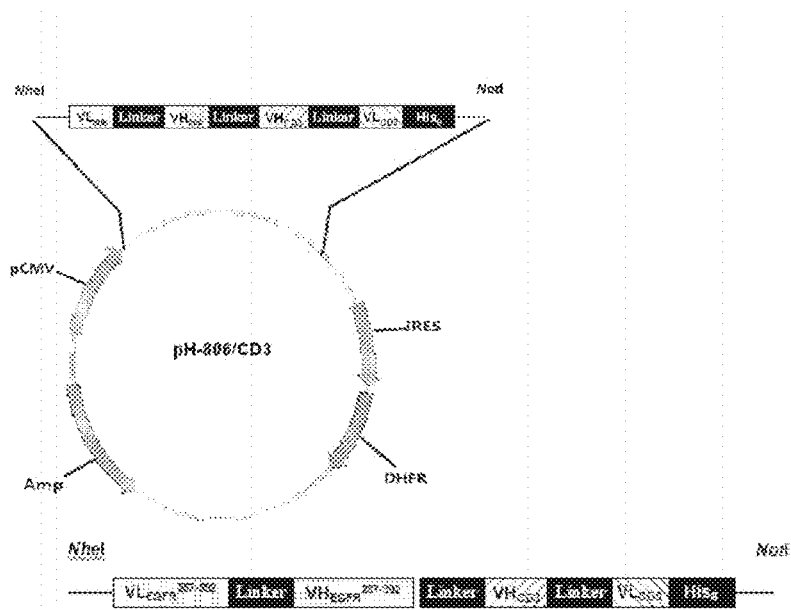
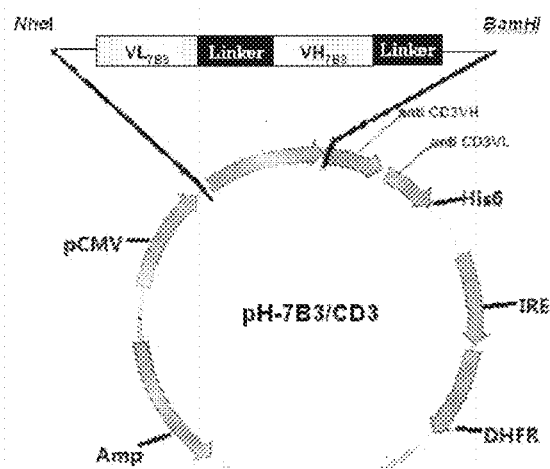
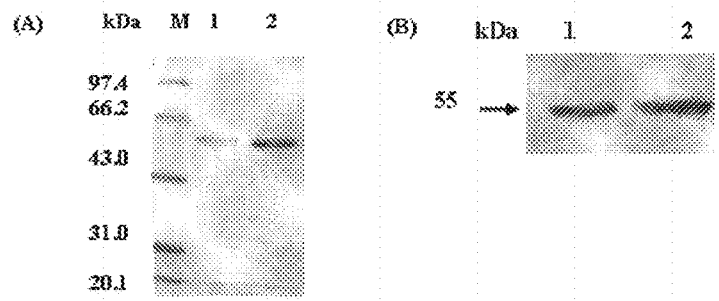
Fig. 3A-3B

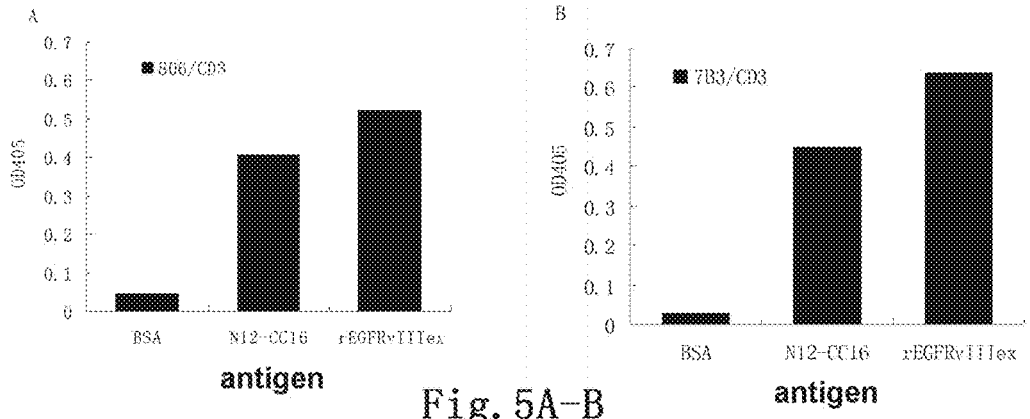
Fig. 5A-B
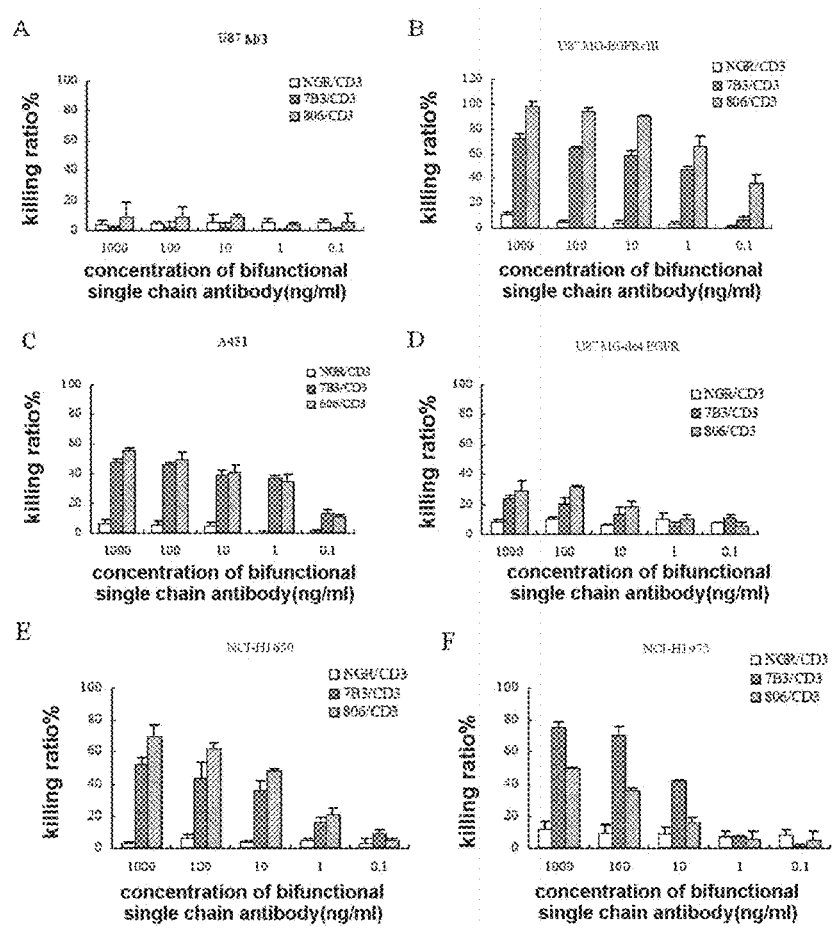
Fig. 6A-6F

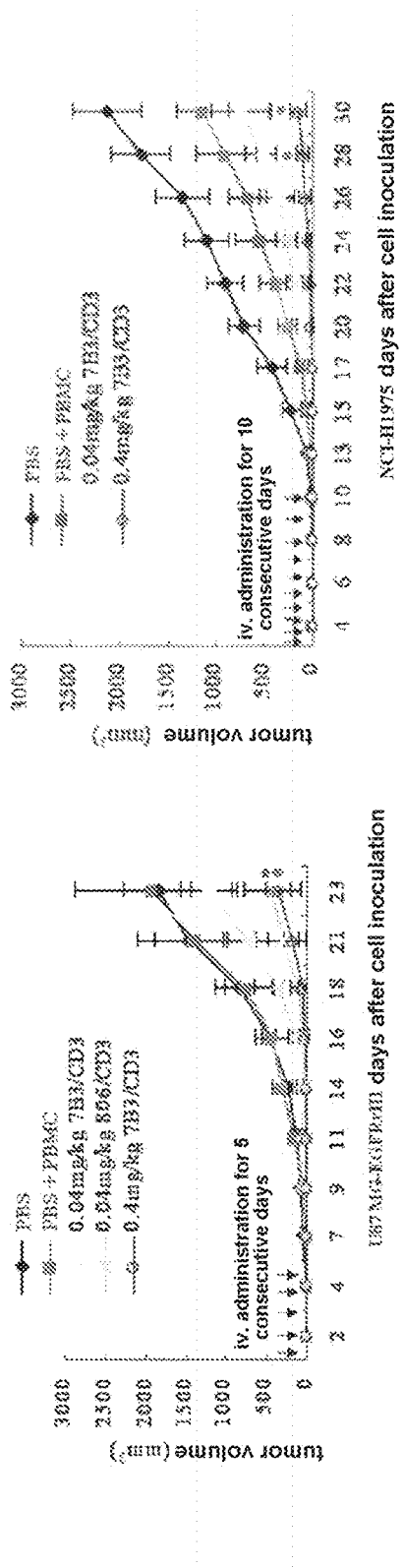
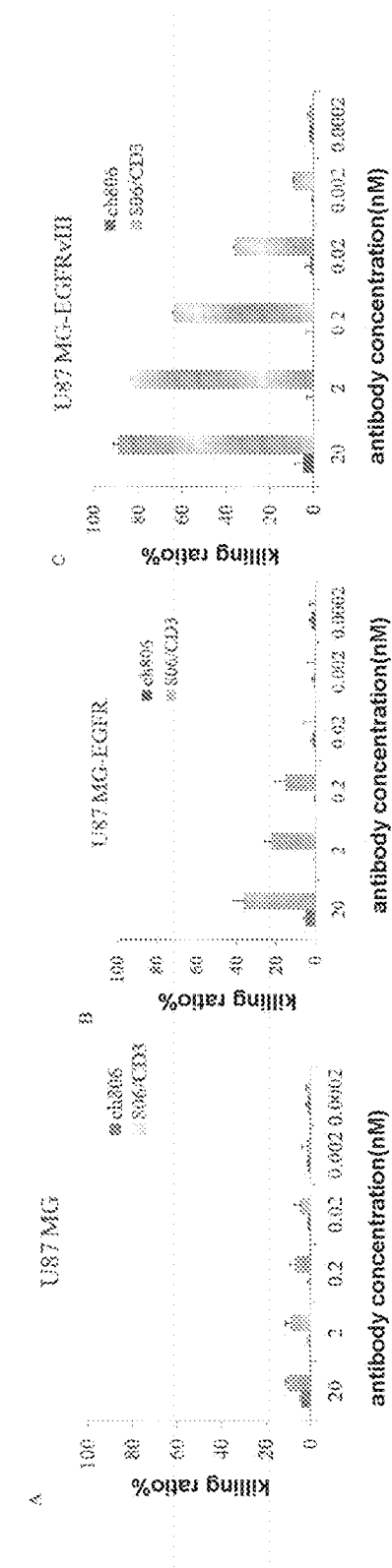

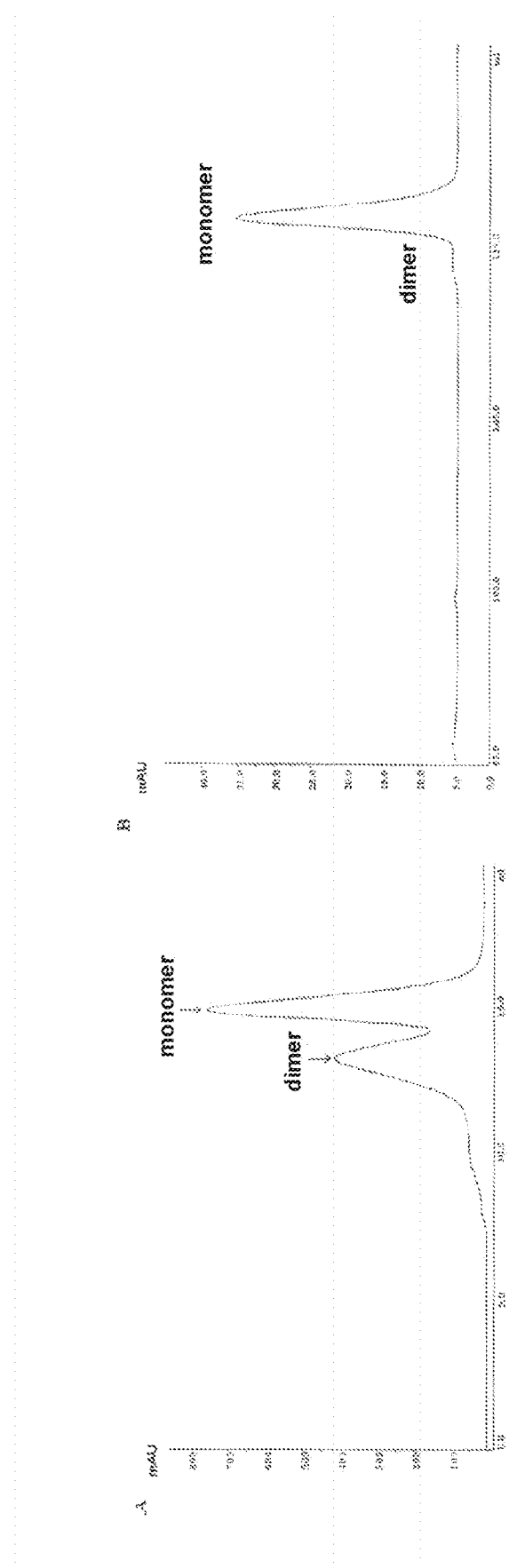
Fig. 10A-B

MULTI-FUNCTIONAL ANTIBODY POLYPEPTIDE FOR CRYPTIC EPITOPE OF EPIDERMAL GROWTH FACTOR RECEPTOR AND T CELL ANTIGEN

PRIORITY

This application is a U.S. National Stage application under 35 U.S.C. § 371 based on International Application No. PCT/CN2013/072098, filed Mar. 4, 2013, which claims priority to Chinese Patent Application No. CN201210094008.X, filed Apr. 1, 2012, the entire contents of each of which are incorporated by reference herein.

TECHNICAL FIELD

The invention relates to the field of biomedicine. More specifically, the invention relates to multi-functional antibody polypeptide that can recognize and bind to a cryptic epitope of epidermal growth factor receptor (EGFR) and T cell antigen. The invention also relates to nucleotide sequence encoding the antibody polypeptide, vector comprising the nucleotide sequence, host cell comprising the vector etc. The invention also relates to the use of the multi-functional antibody polypeptide in preparing an antineoplastic drug and a kit for tumor diagnosis, treatment and/or prevention.

BACKGROUND

EGFR has been demonstrated to be overexpressed in many types of human solid tumors, including lung cancer, colon cancer, breast cancer, gastric cancer, brain cancer, bladder cancer, head and neck carcinoma, ovarian cancer, esophagus cancer, liver cancer, kidney cancer and prostate cancer. The development of antibody drug for the epidermal growth factor receptor family provides an opportunity for the treatment of these tumors.

At least two antibody drugs against EGFR have been used in clinical tumor treatment, for example Erbitux® (also known as Cetuximab) and panitumumab. But the applications of these antibodies have some limitations. This is because on the one hand, EGFR is expressed in many human solid organs such as skin and liver, which may leads to the uptake of the antibody drugs by these organs after they were administered in vivo (Baselga J et al. Phase I studies of anti-epidermal growth factor receptorchimeric antibody C225 alone and in combination with cisplatin. J. Clin. Oncol. 2000 February; 18(4): 904-14, and Faillot T et al. A phase I study of an anti-epidermal growth factor receptor monoclonal antibody for the treatment of malignant gliomas. Neurosurgery. 1996 September; 39(3): 478-83). On the other hand, nonspecific effects of these antibodies on the tissue with normal EGFR expression, may result in the side effects such as skin rash during the administration of antibody drug such as Erbitux (Agero A L, et al, Dermatologic side effects associated with the epidermal growth factor receptor inhibitors. J Am Acad Dermatol. 2006 October; 55(4): 657-70), and some serious side effects can lead to the patient to have to stop taking the drug.

In order to reduce side effects caused by the interaction between the existing EGFR antibodies and normal tissues, several monoclonal antibodies against tumor specific EGFR epitopes were developed, for example, an antibody targeting the junction LEEKKGNY generated by the deletion of 267 amino acids in exons 2-7 of de2-7EGFR (also known as EGFRvIII) (see antibody 131 disclosed in patent application PCT/US2004/020295); antibodies for cryptic epitopes of EGFR such as mAb806 and CH12 (see US patent applications US2011/0076232A1 and WO/2011/035465). When EGFR is activated, overexpressed, or mutated, its cryptic epitope (287CGADSYEMEEDGVRKC302) may be exposed and bind to antibodies such as mAb806 for this epitope (Garrett T P et al., Antibodies specifically targeting a locally misfolded region of tumor associated EGFR. Proc Natl Acad Sci USA. 2009; 106(13): 5082-7). In animal experiments, these antibodies display antitumor effects and show better tumor specificity than other anti-EGFR antibodies developed previously. Human-murine chimeric antibody ch806 which was derived from mAb806 exhibits a strong tumor targeting ability and no obvious skin toxicity was observed in phase I clinical trials (Scott A M, Lee F T et al, A phase I clinical trial with monoclonal antibody ch806 targeting transitional state and mutant epidermal growth factor receptors. Proc Natl Acad Sci USA. 2007 Mar. 6; 104(10): 4071-6). Even at a dose of 5 mg/m$^2$, ch806 displays tumor uptake. For other previous anti-EGFR antibodies, they need about 10 to 20 times of the dose to show tumor uptake (Divgi C R et al. Phase I and imaging trial of indium 111-labeled anti-epidermal growth factor receptor monoclonal antibody 225 in patients with squamous cell lung carcinoma. J Natl Cancer Inst. 1991 Jan. 16; 83(2): 97-104). (Rushika M. Perera, et al. Treatment of Human Tumor Xenografts with Monoclonal Antibody 806 in Combination with a Prototypical Epidermal Growth Factor Receptor Specific Antibody Generates Enhanced Antitumor Activity. Clin Cancer Res 2005; 11(17): 6390-9).

Additionally, the antibodies for above-mentioned epitopes such as CH12 do not show obvious antitumor efficacy on the tumors expressing other forms of EGFR (for instance, T790M mutated EGFR). The T790M mutation often occurs a period of time after the therapy of an EGFR-related lung adenocarcinoma with small molecular tyrosine kinase inhibitors (Xu Y et. al, Acquired resistance of lung adenocarcinoma to EGFR-tyrosine kinase inhibitors gefitinib and erlotinib. Cancer Biol Ther. 2010 April; 9(8): 572-82. Epub 2010 Apr. 26).

Thus, it is valuable to reform these antibodies to increase their antitumor activities (i.e., reduce the minimum effect dose), and expand their antitumor ranges.

One of the interesting ways to increase the antitumor activities of antibody is to construct bifunctional antibody. Bifunctional antibody that specifically recognizes both EGFR and CD3 antigen has been described in the prior art. One part of its functional domain is specific to EGFR and the other part of its functional domain is specific to the CD3 antigen on T cells. Although the bifunctional antibodies made of Cetuximab or Pantitumumab and anti-CD3 antibody display excellent antitumor activities, they show relatively strong toxic effects on the normal cells or tissues with EGFR expression in primate animal experiments (Lutterbuese R, Raum T et. al, T cell-engaging BiTE antibodies specific for EGFR potently eliminate KRAS- and BRAF-mutated colorectal cancer cells. Proc Natl Acad Sci U.S.A. 2010; 107(28): 12605-10).

Due to the nature of complexity of biological experiments, it is not sure whether each functional domain of the prepared bifunctional antibody can retain the original antigen binding specificity and further display the antitumor activity, although technology for the preparation of bifunctional antibody already exists.

This field further requires bifunctional antibody with increased tumor killing biological activity and increased tumor recognition specificity for the EGFR-related tumors. The invention realizes this purpose.

THE CONTENT OF THE INVENTION

The first aspect of the present application relates to a multi-functional antibody polypeptide, comprising (a) a first functional domain, specifically recognizing a cryptic epitope consisting of 287th to 302nd amino acids of EGFR, shown as SEQ ID NO.1, (b) a second functional domain, specifically recognizing the surface antigen of a human T cell.

The second aspect of the present application relates to nucleotide sequence encoding the polypeptide.

The third aspect of the present application relates to a vector comprising the nucleotide sequence.

The fourth aspect of the present application relates to a eukaryotic host cell or prokaryotic host cell comprising the vector.

The fifth aspect of the present application relates to the use of the polypeptide in preparing a drug for the tumor diagnosis, treatment and/or prevention.

The meanings of the terms used in this invention are as follows:

"Specific recognition" and specific degree can be judged by classical immunological techniques, including but not limited to immunoblotting, immunoaffinity chromatography, flow cytometry analysis etc. In the present invention, specific recognition is preferred to be determined by flow cytometry technique, and the standard for the specific recognition in specific circumstances can be judged by skilled person in the art based on the common knowledge they mastered.

"Functional domain" refers to the antibody or antibody fragment that can specifically recognize an antigen, including intact antibody, single chain antibody (scFV), Fd fragment, Fab fragment, F (ab')$_2$ fragment, single domain antibody fragment, separated CDR fragment, and derivatives thereof.

"Intact antibody" consists of two same heavy chains and two same light chains, each chain includes a variable region (V region) and one or more constant region(s) (C region). Variable region is responsible for antigen binding, while the constant region is mainly responsible for binding effector molecules. There are three flexible rings with high diversity in the variable region, called the complementarity determining region (CDR), which is mainly responsible for the recognition of antigen. The other part of the variable region comprises the rigid 0 sheet supporting so-called framework regions (FRs). CDR and FR are arranged at intervals to form a sandwich structure.

"Single chain Fv (scFV) fragments" refers to the antibody fragments constructed by gene engineering, which is a recombinant protein composed of a heavy chain variable region ($V_H$) and a light chain variable region ($V_L$) connected by a linker which makes the two domains correlated with each other to form the antigen binding sites. Generally, the size of the ScFV is ⅙ of an intact antibody.

"Fd fragment" refers to antibody fragments composed of a heavy chain $V_H$ and $C_{H1}$.

"Fab fragment" refers to a heterodimer composed of a Fd fragment (composed of a heavy chain $V_H$ and $C_{H1}$) and the intact light chain linked by disulfide bonds between the chains. The size of a "Fab antibody" is about ⅓ of an intact antibody, which comprises only one antigen binding site.

"F (ab')$_2$ fragment" refers to a bivalent fragment comprising two connected Fab fragments.

"Single domain antibody" is composed of a heavy chain variable region or a light chain variable region. The name was made because the antibody fragment consists of only one domain. The size of the fragment is about 1/12 of an intact antibody.

"Antibody derivatives" includes for example when the antibody derivatives is obtained by phage display technology, surface plasmon resonance technology used in BIA-CORE system can be used to increase the efficiency of the phage antibody bound to EGFR or CD3 antigen epitope (Schier, Human antibody hybridoma 7(1996), 97-105; Malmborg, Journal of immunology methods 183 (1995), 7-13). Also includes, for example the method for generating chimeric antibodies described in WO 89/09622, the method for generating humanized antibodies described in EP-A10239400 and WO90/07861, the method for generating xenogeneic antibodies such as human antibody using the mice described in WO91/10741, WO94/02602 and WO96/33735.

The antibody or its fragments used in the present invention can be further modified with the conventional technologies known in the field alone or in combination, such as amino acid deletion, insertion, substitution, addition, and/or recombination and/or other modification methods. It is well known for the skilled person in the art to introduce this modification into the DNA sequence of the antibody according to its amino acid sequence; see for example, Sambrook, molecular cloning: a laboratory manual, Cold Spring Harbor Laboratory (1989) N.Y. The modification is preferably conducted at the nucleic acid level.

The antibody or its antibody fragments of the present invention can be humanized, chimeric or mouse originated.

BRIEF DESCRIPTION OF DRAWINGS

FIG. 1. The upper half part is the structural schematic diagram of pH-806/CD3 expressing vector while the lower half part is the enlarged schematic diagram for the inserted gene fragments.

FIG. 2. Structural schematic diagram of pH-7B3/CD3 expressing vector.

FIG. 3A. Sodium dodecyl sulfate-polyacrylamidegelelectrophoresis (SDS-PAGE) assay for the purified bifunctional antibody polypeptide, M represents molecular weight marker (low molecular weight protein standard for SDS-PAGE is provided by the Shanghai Shengzheng Biological Technology Co. Ltd). The first lane is 806/CD3 while the second lane is 7B3/CD3.

FIG. 3B. Western blot assay for the purified bifunctional antibody polypeptides. The first lane is 806/CD3 while the second lane is 7BC3/CD3.

FIG. 5A. Analysis of the antigen-binding epitope of 806/CD3 (ELISA).

FIG. 5B. Analysis of the antigen-binding epitope of 7B3/CD3 (ELISA).

FIG. 6A. Comparison of the killing ratio of the T cells on U87 MG cancer cells induced by a serial gradient dilutions of the three bifunctional single chain antibodies (NGR/CD3, 7B3/CD and 806/CD3).

FIG. 6B. Comparison of the killing ratio of the T cells on U87 MG-EGFRvIII cancer cells induced by a serial gradient dilutions of the three bifunctional single chain antibodies (NGR/CD3, 7B3/CD and 806/CD3).

FIG. 6C. Comparison of the killing ratio of the T cells on A431 cancer cells induced by a serial gradient dilutions of the three bifunctional single chain antibodies (NGR/CD3, 7B3/CD and 806/CD3).

FIG. 6D. Comparison of the killing ratio of the T cells on U87 MG-de4 EGFR cancer cells induced by a serial gradient dilutions of the three bifunctional single chain antibodies (NGR/CD3, 7B3/CD and 806/CD3).

FIG. 6E. Comparison of the killing ratio of the T cells on NCI-H1650 cancer cells induced by a serial gradient dilutions of the three bifunctional single chain antibodies (NGR/CD3, 7B3/CD and 806/CD3).

FIG. 6F. Comparison of the killing ratio of the T cells on NCI-H1975 cancer cells induced by a serial gradient dilutions of the three bifunctional single chain antibodies (NGR/CD3, 7B3/CD and 806/CD3).

FIG. 7. Antitumor activity assays for the treatment groups using different concentrations of bifunctional antibodies (7B3/CD3 and 806/CD3) and the control groups in NOD/SCID mice bearing tumors (U87 MG-EGFRvIII).

FIG. 8. Antitumor activity assays for the treatment groups using different concentrations of bifunctional antibodies (7B3/CD3) and the control groups in NOD/SCID mice bearing tumors (NCI-1975).

FIGS. 9A-9C. Comparison of the killing ratio of 806/CD3 and ch806 on three different cancer cell lines.

FIGS. 10A-B. Gel filtration chromatography curves of the genetic-engineering expressed 806/CD3 bifunctional antibody.

DETAIL DESCRIPTION OF THE INVENTION

Figures 4A, 4B, 4C, 4D, 4E, 4F, 4G, 4H:
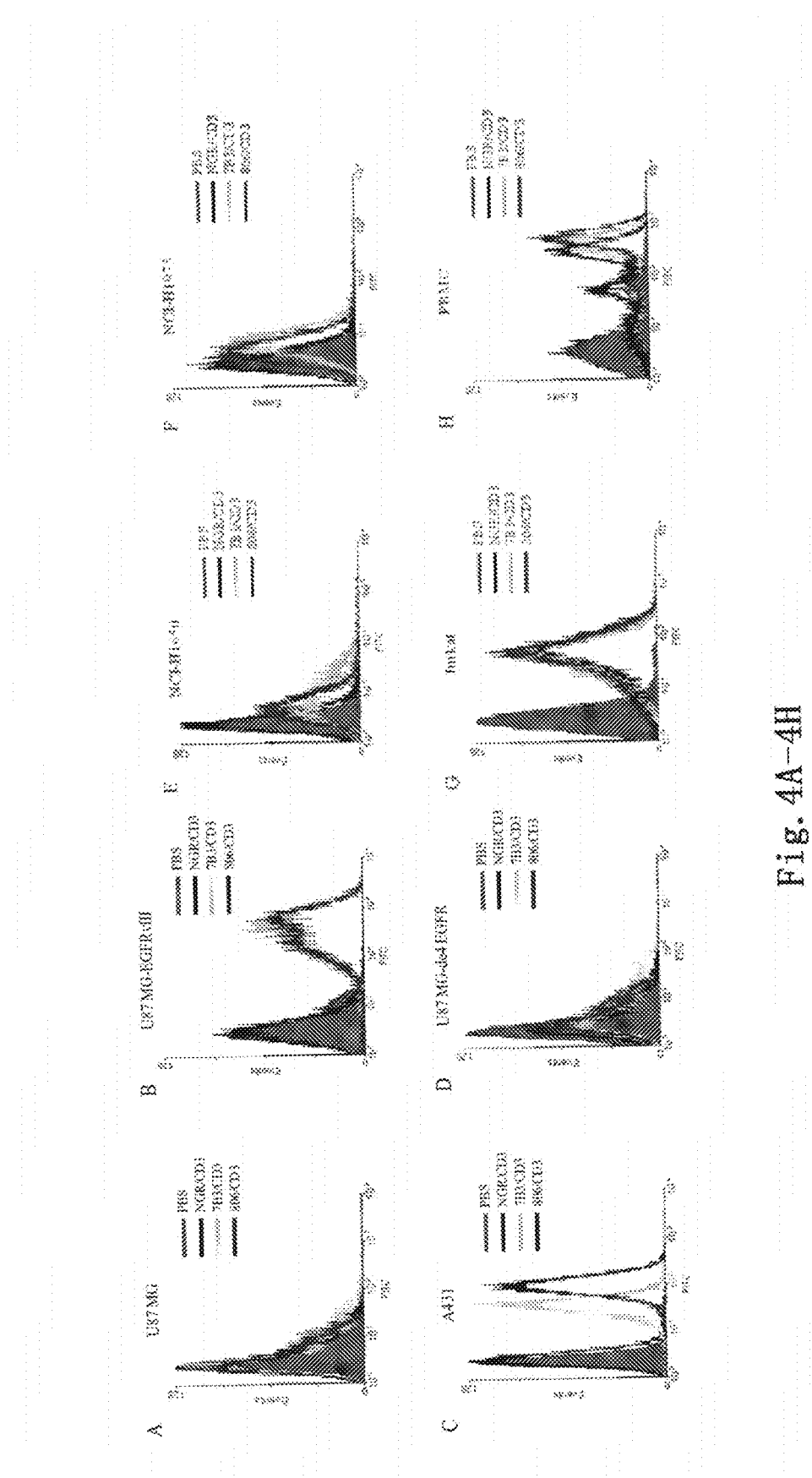
FIG. 4A. The specific binding assay for the three bifunctional single chain antibodies (NGR/CD3, 7B3/CD3 and 806/CD3) and U87MG cancer cells determined by Fluorescence Activated Cell Sorter (FACS).
FIG. 4B. The specific binding assay for the three bifunctional single chain antibodies (NGR/CD3, 7B3/CD3 and 806/CD3) and U87 MG-EGFRvIII cancer cells determined by FACS.
FIG. 4C. The specific binding assay for the three bifunctional single chain antibodies (NGR/CD3, 7B3/CD3 and 806/CD3) and A431 cancer cells determined by FACS.
FIG. 4D. The specific binding assay for the three bifunctional single chain antibodies (NGR/CD3, 7B3/CD3 and 806/CD3) and U87 MG-de4 EGFR cancer cells determined by FACS.
FIG. 4E. The specific binding assay for the three bifunctional single chain antibodies (NGR/CD3, 7B3/CD3 and 806/CD3) and NCI-H1650 cancer cells determined by FACS.
FIG. 4F. The specific binding assay for the three bifunctional single chain antibodies (NGR/CD3, 7B3/CD3 and 806/CD3) and NCI-H1975 cancer cells determined by FACS.
FIG. 4G. The specific binding assay for the three bifunctional single chain antibodies (NGR/CD3, 7B3/CD3 and 806/CD3) and Jurkat cancer cells determined by FACS.
FIG. 4H. The specific binding assay for the three bifunctional single chain antibodies (NGR/CD3, 7B3/CD3 and 806/CD3) and PBMC cells determined by FACS.

The invention provides a multi-functional antibody against a series of tumors. The series of tumors include tumors with amplified EGFR genes and tumors expressing mutated EGFR such as de2-7 EGFR with the deletion of the exons 2-7. The tumors included but not limited to lung cancer, colon cancer, breast cancer, gastric cancer, brain cancer, bladder cancer, head and neck carcinoma, ovarian cancer, kidney cancer and prostate cancer. The multi-functional antibody comprises a functional domain that specifically recognizing a cryptic epitope comprising the amplified EGFR genes or consisting of 287th to 302nd amino acids of EGFR expressed by tumors with mutated EGFR genes, shown as SEQ ID NO: 1, and a second functional domain recognizing the surface antigen of a human T cell.

Multi-functional antibody of the invention can induce T cell cytotoxicity on cancer cells in vitro and in vivo at very low concentrations, such as from 100 pg/mL to 1 ng/ml. Even at a relatively low effector cell (E):Target cell (T) ratio, such as 10:1, the specific lysis of the related cancer cell lines can be observed without requiring any kind of pre-stimulation on T cells. The related cancer cell lines for the present invention including the above cancer cells expressing EGFR mutants such as de2-7EGFR or expressing amplified EGFR can be obtained from commercial sources. For example, NCI-1650, NCI-1975, A431 were obtained from American Type Culture Collection (ATCC). Another example is U87 MG-EGFRvIII, which is U87 MG cell line with stable EGFRvIII expression, its construction method was shown in literature (Jiang H, J Biol. Chem., 2011, 286(7): 5913-20). U87 MG also can be obtained from ATCC.

In addition, the multi-functional polypeptide of this invention hardly binds to cells (for instance U87 MG) without EGFR amplification or mutation. An antitumor drug developed from the multi-functional polypeptide of the invention has improved tumor targeting and less cytotoxic activities on normal tissues in vivo.

The first functional domain of this invention recognizes the cryptic epitope formed by the amino acid sequence shown as SEQ ID NO:1. Antibodies that can specifically recognize said cryptic epitope (for instance the epitope included in the 287th to 302nd amino acids in human wild type EGFR) have been disclosed, for example, mAb806 and the derived antibody thereof in America patent application US2011/0076232A1 and WO/2011/035465, and antibody 12H23 and said the derived antibody thereof in Chinese patent application CN101602808A. Additionally, the preparation of other specific antibodies against the above cryptic epitope can be performed according to the methods known in the field. The first functional domain of the invention can bind specifically to the tumors expressing multi-copy EGFRs or EGFR mutants such as de2-7EGFR.

The second functional domain of the invention includes antibodies and antibody fragments specifically recognizing T cell antigens. The T cell surface antigens include, but not limited to CD3, CD16, CD28. Preferably, the T cell surface antigen is CD3. CD3 is an antigen expressed by T cells. It is a part of multi-molecule T cell receptor complex (TCR), comprising three different chains CD3ε, CD3 δ, CD3 γ. The CD3 cluster on T cells (for example by immobilized anti-CD3 antibody) can lead to T cell activation which is similar to the binding of T cell receptor, but is not dependent on the specific type of its clones. Actually, CD3ε is the chain recognized by most of the anti-CD3 antibodies. The bifunctional antibody kills tumor cells mainly by stimulating the immune system without being limited by major histocompatibility antigen (MHC). The killing effects on tumor cells can be obtained when the anti-CD3 antibody part in the bifunctional antibody binds to the CD3 on the T cell surface.

In one embodiment of the invention, the first functional domain comprises at least one complementarity determining region (CDR) of the anti-EGFR antibody heavy chain variable region selected from the following sequences: SEQ ID NO. 2, SEQ ID NO. 3 and SEQ ID NO. 4. Preferably, the first functional domain is the heavy chain variable region comprising the above three CDRs in order.

In another embodiment of the invention, the first functional domain comprises at least one complementarity determining region (CDR) of the anti-EGFR antibody light chain variable region selected from the following sequences: SEQ ID NO. 5, SEQ ID NO. 6 and SEQ ID NO.7. Preferably, the first functional domain is the light chain variable region comprising sequentially the above three CDRs.

More preferably, the first functional domain is a single chain anti-EGFR monomer comprising the above-mentioned whole heavy chain variable region and the whole light chain variable region sequentially connected together.

In another embodiment of the invention, the second functional domain is a single chain anti-CD3 antibody.

The two functional domains in the multi-functional antibody of the invention can comprise two different single chain antibodies. Thereby, the antibody can also be called single chain bifunctional antibody. In one embodiment, the bifunctional antibody polypeptide has the amino acid sequence shown in SEQ ID NO. 8. In another embodiment, the bifunctional antibody polypeptide has an amino acid sequence shown in SEQ ID NO. 9.

In another embodiment of the present invention, the polypeptide further comprises a linker located between the first and second functional domains or located between different complementarity determining regions inside the first or second functional domain. The polypeptide linker preferably includes several hydrophilic peptide bond amino acids, the length of which is sufficient to cross the distance between the C terminus of the functional domain with the binding site and the N terminus of another functional domain with the binding site. Therefore, when in aqueous solutions, the multi-functional antibody of the invention can show conformation suitable for binding. Preferably, the polypeptide linker comprises a plurality of glycine, alanine and/or serine residues. In a specific preferred example of the invention, the amino acid sequence of the polypeptide linker is (GlyGlyGlyGlySer)n, where n is an integer from 1 to 5, preferably from 1 to 3, more preferably n is 3.

When each of the first and second functional domains comprises two or more variable regions ($V_H$, $V_L$), the variable regions are preferably connected by the above-mentioned polypeptide linker. The amino acid sequence of the polypeptide of the invention for linking the polypeptide linker is (GlyGlyGlyGlySer)n, where n is an integer from 1 to 5, preferably from 1 to 3, more preferably n is 1.

The first and second functional domains of the antibody in the present invention can be a pair of VH-VL, VH-VH, or VL-VL domains from the same or different antibodies. The order of the VH and VL functional domains of the invention is not determined. When the order is reversed, the function loss will generally not happen. Importantly, the arrangement of the VH and VL domains enables the correct folding of the antigen-binding sites, thus the multi-functional antibody that formed has the function to specifically recognize and bind to multiple antigens.

In a preferred example of the polypeptide of the invention, the arrangement sequence of the functional domains is $VL_{EGFR}$-$VH_{EGFR}$-$VH_{CD3}$-$VL_{CD3}$.

Another aspect of the present invention relates to the nucleotide sequence of the above-mentioned polypeptide. In one embodiment, it relates to the nucleotide sequence of SEQ ID NO. 10 encoding the amino acid sequence of the SEQ ID NO. 8. In another embodiment, it relates to the nucleotide sequence of SEQ ID NO. 11 encoding the amino acid sequence of the SEQ ID NO. 9.

Another aspect of the present invention relates to vectors comprising nucleotide sequences encoding the above-mentioned polypeptides. The vector may be eukaryotic or prokaryotic cell vector, as long as the vector meets: (a) its coding sequence comprises replication initiation sequence enabling its replication in the host cell, (b) it comprises gene sequence encoding selective markers, the encoded protein of which is essential for the host cells to survive and grow in a specific selection medium. Without transfection or transformation of the vector comprising said gene in the host cells, they cannot survive in specific selection medium. Typical proteins encoded by selective marker genes include proteins resistant to antibiotics or toxins (includes ampicillin, kanamycin, tetracycline, neomycin, hygromycin, and methotrexate, etc.); and proteins (for example, protein coded by D-alanineracemase gene) that can compensate auxotrophic condition and supply key nutrients which is absent in the medium. Examples using resistance screening include transfection of exogenous vector comprising neomycin resistance gene which enables the host cells surviving and growing in medium containing neomycin or G418. Another example is the use of dihydrofolate reductase (DHFR) selective marker in mammalian cells such as Chinese hamster ovary cells (CHO). Mammalian host cells refer to DHFR auxotrophic cells lacking dihydrofolate reductase gene which are unable to synthesize nucleic acids and must be grown in the medium containing HT. When host cells are transfected with vectors, positive clones with exogenous vectors carrying both target gene and DHFR gene can be selected and obtained by the above-mentioned medium conditions. (c) Its coding sequence comprises a promoter sequence, (d) expression vector may also comprise other component sequences, including signal peptide sequence, transcription termination sequence, enhancer sequence etc. Preferably, the vector of the present invention is eukaryotic expression vector. Preferably, the vector of the present invention is pH vector used for eukaryotic antibody expression, which comprises elements such as CMV promoter, internal ribosome entry site (IRES) sequence, DHFR screening marker etc. Methotrexate (MTX) is an inhibitor of DHFR, which can block its function. When the cell culture medium comprises MTX, DHFR is inhibited, which makes the gene self-amplification by feedback regulation, as well as the amplifications of its upstream and downstream genes. Thus, the target gene is also amplified and the yield of the target protein is increased.

Another aspect of the present invention relates to the host cells comprising the vectors for the expression of the multi-functional antibody polypeptide in need. Compatible with the used vectors, host cells of the present invention can be any prokaryotic or eukaryotic host cells. Eukaryotic host cells, including yeast, insect cells, plant cells, mammalian cells may be preferred, because eukaryotic cells have complex target protein post-translational modifications (such as glycosylation) and are being used more and more in large scale culture. The host cell lines commonly used include monkey kidney cells (COS-7 ATCC CRL 1651), human embryonic kidney cell 293 and its subclone cell lines, baby hamster kidney cells (BHK, ATCC, CCL10), China hamster ovary cells (CHO) etc. Preferably, the eukaryotic host cells of the invention are CHO cells.

Another aspect of the present invention relates to the use of the multi-functional antibody polypeptide in preparing a drug for tumor treatment, diagnosis and/or prevention.

EXAMPLES

Example 1

Amplification of the Single Chain Antibody Sequence Against the Cryptic Epitope Consisting of 287th to 302nd Amino Acids of Human EGFR and the Single Chain Antibody Sequence Against Human CD3

1.1 Amplification of the VH and VL Sequences of the Single Chain Antibody Against the Cryptic Epitope Consisting of 287th to 302nd Amino Acids of Human EGFR The single chain antibody against the cryptic epitope consisting of 287th to 302nd amino acids of human EGFR can be 1) VH and VL of antibody 806 whose nucleotide sequences were shown respectively in SEQ ID No.1 and SEQ ID NO.3 in U.S. Pat. No. 7,589,180B2, or 2) VH and VL of antibody 7B3 whose nucleotide sequences were shown in SEQ ID NO.13 and SEQ ID NO.14 respectively.

The VL and VH genes of antibody 806 were obtained by PCR method. The VL gene was obtained by primer 5'L806-2 and 3'L806 while the VH gene was obtained by primer 5'H806 and 3'H806.

The VL or VH genes of antibody 7B3 were obtained by the PCR method respectively. The VL gene was obtained by primer 5'L7B3-2 and 3'L7B3 while the VH gene was obtained by primer 5'H7B3 and 3'H7B3.

Primers for the amplification of VL region of antibody 806:

5'L806-2:
(SEQ ID NO. 15)
gttgctttggtttccaggtgcaagatgtgacatcctgatgaccca

3'L806:
(SEQ ID NO. 16)
ccgccagagccacctccgcctgaaccgcctccaccacgtttgatt
tccagcttgg Primers for the amplification of VH region of antibody 806:

5'H806:
(SEQ ID NO. 17)
gcggaggtggctctggcggtggcggatcgg
ccgatgtgcagcttcagga

3'H806:
(SEQ ID NO. 18)
ggatccaccacctcctgcagagacagtgac

Primers for the amplification of VL region of antibody 7B3:

5'L7B3-2:
(SEQ ID NO. 19)
gttgctttggtttccaggtgcaagatgtgatattcagatgacc

3'L7B3:
(SEQ ID NO. 21)
acctccgcctgaaccgcctccacctgaacgtttaatttccac

Primers for the amplification of VH region of antibody 7B3:

5'H7B3:
(SEQ ID NO. 22)
ttcaggcggaggtggctctggcggtggcggatcggatgtgcagctg

3'H7B3:
(SEQ ID NO. 23)
ggatccaccacctccgctgctcacggtcac 1.2 Amplification of VH and VL Sequences of Single Chain Antibody Against Human CD3:

The nucleotide sequences of VH and VL genes of mouse-anti-human CD3 antibody against human CD3 were obtained from the sequences shown as SEQ ID NO. 9 (847-1203) and SEQ ID NO.9 (1258-1575) in U.S. Pat. No. 7,112,324B1. The nucleotide sequences of the VL and VH domains of the antibody against human CD3 were amplified by PCR methods, and the following primers were used:

Primers for the amplification of VH region of the antibody against human CD3:

5'HCD3:
(SEQ ID NO. 24)
ggaggtggtggatccgatatcaaactgcagc

3'HCD3:
(SEQ ID NO. 25)
cacttccaccagaacctccacttccaccttcgactgaggagactgtgag

Primers for the amplification of VL region of the antibody against human CD3:

5'LCD3:
(SEQ ID NO. 26)
ctggtggaagtggaggttcaggtggagtcgacgacattcagc

3'LCD3:
(SEQ ID NO. 27)
ctatgcggccgcctaatgatgatggtgatgatgtttcagctcca

Example 2

The Construction of the Expression Vector Comprising Nucleotide Sequences Encoding Single Chain Bifunctional Antibody 806/CD3

VL806-linker 1-VH806-linker 2 was obtained by fusion-PCR amplification using the above PCR-amplified nucleotide sequences of VH and VL regions of antibody 806 and the nucleotide sequences encoding the linker 1 amino acids (GlyGlyGlyGlySer)$_3$ and encoding the linker 2 amino acids (GlyGlyGlyGlySer); while the VH$_{CD3}$-linker 3-VL$_{CD3}$ was obtained by fusion-PCR amplification using the above PCR-amplified nucleotide sequences of VH and VL regions of the antibody against human CD3 and the nucleotide sequence encoding the linker 3 amino acids VE(GGS)$_4$GG.

Then the above amplified products were amplified by fusion-PCR to obtain single chain bifunctional antibody with the following connection order:

[VL$_{806}$-linker 1-VH$_{806}$-linker 2-VH$_{CD3}$-linker 3-VL$_{CD3}$]

The third round amplification was then performed using the linked sequence ([VL$_{806}$-linker 1-VH$_{806}$-linker 2-VH$_{CD3}$-linker 3-VL$_{CD3}$]) with the following primers to introduce a signal peptide sequence and a site for the restriction endonuclease NheI into the N terminus, as well as to introduce a His-tag and a site for the restriction endonuclease NotI into the C terminus.

5'L806-1:
(SEQ ID NO. 28)
ctagctagccaccatggtgtccacagctcagttccttgcattct
tgttgctttggtttc -continued 3'LCD3:
(SEQ ID NO. 27)
ctatgcggccgcctaatgatgatggtgatgatgtttcagctcca The amplified sequence SEQ ID NO: 10 was digested with restriction endonucleases NheI/NotI-HF simultaneously, according to the reaction condition (buffer 2) recommended by the enzyme manufacturer (New England Biolabs, NEB). The pH expression vector (shown in example 7 and FIG. 15 of WO/2011/035465) was also digested with restriction endonucleases NheI/NotI-HF simultaneously. After that, T4 DNA ligase was used to link the digested SEQ ID NO: 10 fragment and the pH/DHFR vector fragment according to the reaction condition recommended by the enzyme manufacturer (NEB). Thus, the nucleotide sequence encoding the single chain bifunctional antibody 806/CD3 was cloned into the vector. The obtained new vector comprising the single chain bifunctional antibody 806/CD3 peptide was named as pH/806/CD3; its detailed structure was shown in FIG. 1.

Example 3

Construction of the Expression Vector Comprising the Nucleotide Sequences Encoding Bifunctional Antibody 7B3/CD3

$VL_{7B3}$-linker 1-$VH_{7B3}$-linker 2 was obtained by fusion-PCR amplification using the above PCR-amplified nucleotide sequences of VH and VL regions of antibody 7B3 and the nucleotide sequences encoding the linker 1 amino acids (GlyGlyGlyGlySer)$_3$ and encoding the linker 2 amino acids (GlyGlyGlyGlySer); while the $VH_{CD3}$-linker 3-$VL_{CD3}$ was obtained by fusion-PCR amplification using the above PCR-amplified nucleotide sequences of VH and VL regions of the antibody against human CD3 and the nucleotide sequence encoding the linker 3 amino acids VE(GGS)$_4$GG.

The above linked sequences ($VL_{7B3}$-linker 1-$VH_{7B3}$-linker 2) were then further amplified using the primers shown in SEQ ID NOs: 20 and 29 to introduce a signal peptide sequence and a NheI site into the N terminus, as well as to introduce a BamHI site into the C terminus. The further amplified sequence (SEQ ID NO: 12) was digested with NheI and BamHI in buffer 2 according to the reaction condition recommended by the enzyme manufacturer (NEB).

5'L7B3-1:
(SEQ ID NO. 20)
ctagctagccaccatggtgtccacagctcagttccttgcattct
tgttgctttggtttc 3'H7B3-2:
(SEQ ID NO. 29)
tcttgccagttcagccctgactgctgcagtttgatatcggatc
caccacctccg The vector pH-806/cd3 constructed in example 2 was digested with the same NheI and BamHI. The longer fragment obtained after digestion was linked with SEQ ID NO: 12. Thus, the nucleotide sequence (SEQ ID NO: 11) encoding single chain bifunctional antibody 7B3/CD3 peptide was cloned into the vector. The resulted new vector was named as pH-7B3/CD3; its detailed structure was shown in FIG. 2.

Example 4

Expression and Purification of Single Chain Bifunctional Antibody 806/CD3 and 7B3/CD3

The expression vectors pH-806/CD3 and pH-7B3/CD3 were transfected into CHO cells according to procedures described in the manual of the transfection reagents (FreeStyle MAX Reagent, purchased from Invitrogen). Stable clones were then screened using the OptiCHO™ protein expression kit (purchased from Invitrogen). The stale CHO cell clones comprising one of the above-mentioned expression vectors were incubated at 37° C. in a shaking flask for 7 days with a speed of 130 rpm. The medium used is CD OptiCHO (purchased from Gibco). The supernatant was obtained by centrifugation and stored at −20° C.

According to the methods and procedures provided by the manufacturer, a histidine affinity chromatography column (His Trap HP column, purchased from GE Healthcare) was used to purify the proteins. Specifically, the column was balanced with buffer A (20 mM sodium phosphate, pH 7.4, 0.4 M NaCl). After PBS dialysis, the cell culture supernatant (500 mL of supernatant) was added into the chromatographic column (1 mL) with a flow rate of 3 ml/min. Then 5 times of the volume of the buffer A and 10 times of the volume of the 50 mM imidazole-containing buffer A were used to clean the column and remove impurity proteins. The same buffer A containing 250 mM imidazole was used to elute the binded target proteins. All purification steps were performed at 4° C.

The purified 806/CD3 and 7B3/CD3 proteins were detected by reducing SDS-PAGE. As shown in FIG. 3A, molecular weights of the two single chain bifunctional antibody molecules are both about 60 kD, conforming to the molecular weights calculated according to the amino acid sequences of 806/CD3 and 7B3/CD3.

Furthermore, protein hybridization (Western blot) on the purified proteins was performed using the anti-histidine antibody. The results shown in FIG. 3B indicate that all the resulted proteins have His-tag and their molecular weights are about 60 kD.

The concentrations of 806/CD3 and 7B3/CD3 in the supernatant of transfected CHO cells detected by ELISA are about 3 mg/L. The concentration of purified protein detected at a wavelength of 280 nm is 0.5 mg/L.

Monomers and polymers of the single chain bifunctional antibodies obtained by one-step histidine affinity chromatography column purification method were further separated using gel filtration chromatography. Specifically, prepacked column Superdex 200 10/300 GL (purchased from GE Healthcare) was balanced with PBS buffer (2 times the column volume), 500 µL sample was loaded by loading ring with a flow rate of 0.4 ml/min and then eluted with 1 time volume of PBS. Results as shown in FIG. 10A indicate that the peak value of dimeric proteins appears at 13 ml while the peak value of monomeric protein appears at 15 ml. The purity of the monomeric protein was determined by gel filtration chromatography according to above-mentioned concrete steps. The results shown in FIG. 10B indicate that its purity is greater than 95%.

Example 5

Analysis of the Antigen-Binding Specificity and the Binding Epitope of the Bifunctional Antibody 5.1 Analysis of the Antigen-Binding Specificity The binding capacities of single chain bifunctional antibodies 7B3/CD3 and 806/CD3 to EGFR were determined by FACS (also named as flow cytometer) (FACScalibur, BD).

The concrete procedures are as follows:

1. The tumor cells at logarithmic growth phase listed in Table 1 were inoculated into 6 cm dish with a inoculum density about 90%, and then cultured in 37° C. incubator overnight.

2. The cells were digested with 10 mM of EDTA and collected by centrifugation at 200 g for 5 min. The cells were then resuspended at a concentration about $1\times10^6$-$1\times10^7$/mL in phosphate buffer solution containing 1% fetal calf serum (NBS PBS) and then added into flow tubes at 100 ul/tube.

3. The tubes were then centrifuged at 200 g for 5 min. The supernatant was discarded.

4. In the two experimental groups, 7B3/CD3 and 806/CD3 antibodies were added while in a control group, NGR/CD3 was added as a negative control. PBS blank control without antibody addition was set as another control. The final concentration of each antibody was 20 µg/ml with 100 ul per tube. The tube was bathed in ice for 45 minutes.

5. 2 ml of 1% NBS PBS was added into each tube and then centrifuged at 200 g for 5 min. This step was done twice.

6. After the supernatant was discarded, mouse anti-his-tag antibody (purchased from Shanghai Genomics, Inc) diluted at 1:50 was added with 100 ul per tube. The tube was bathed in ice for 45 min.

7. 2 ml of 1% NBS PBS was added into each tube and then centrifuged at 200 g for 5 min. This step was done twice.

8. After the supernatant was discarded, FITC fluorescent labeled goat anti-mouse antibody (purchased from Shanghai Kangchen Bio-tech Co., Ltd) diluted at 1:50 was added with 100 ul per tube. The tube was bathed in ice for 45 min.

9. 2 ml of 1% NBS PBS was added into each tube and then centrifuged at 200 g for 5 min. This step was done twice.

10. After the supernatant was discarded, the cells were resuspended at 300 ul of 1% NBS PBS and detected by FACS.

11. Flow cytometry data analysis software WinMDI 2.9 was used to analyze the data.

As shown in FIGS. 4B-4C of the present invention, the fluorescence peak of bifunctional antibody 7B3/CD3 shown in green and the fluorescence peak of bifunctional antibody 806/CD3 shown in blue had significant differences when compared to the negative control (NGR/CD3) and blank control (PBS), suggesting both of them could high efficiently bind to U87 MG-EGFRvIII and A431 cells. As shown in FIGS. 4D-4F, the two bifunctional antibodies of the present invention also can bind to U87 MG-de4 EGFR, NCI-1650 and NCI-1975, but with a less binding efficiency than that of U87 MG-EGFRvIII or A431.

As shown in FIG. 4A, these two antibodies (7B3/CD3 and 806/CD3) hardly bound to U87 MG cells. These results suggest that 7B3/CD3 and 806/CD3 can specifically bind to cancer cells expressing human EGFR mutants or overexpressing EGFR while hardly bind to tissues with normal EGFR expression.

As shown in FIG. 4G, the bifunctional antibodies (7B3/CD3 and 806/CD3) of the present invention and the negative control antibody (NGR/CD3) can efficiently bind to Jurkat cells (human peripheral blood leukemia T cell) expressing CD3 substantially at the same level. As shown in FIG. 4H, the bifunctional antibodies (7B3/CD3 and 806/CD3) of the present invention and the negative control antibody (NGR/CD3) can efficiently bind to human peripheral blood mononuclear cells (PBMC) at a similar level. FIGS. 4G and 4H suggest that the 7B3/CD3 and 806/CD3 bifunctional antibodies of the present invention can bind specifically to CD3 antigen on the T cell surface.

Taken together, FIGS. 4A-4H indicate that the bifunctional antibodies (7B3/CD3 and 806/CD3) of the present invention can not only specifically bind to cancer cells expressing human EGFR mutants or over-expressing EGFR, but also bind specifically to the effector cells (T cells) expressing CD3.

5.2 Analysis of the Antigen-Binding Epitope

Prior art literature suggests that monoclonal antibody 806 (mAb 806) can bind to EGFR cryptic epitope peptide, CC16 ($^{287}$CKGYEDSRVMEAGDEC$^{302}$) (Johns T G, et al., J. Biol. Chem. 2004; 279(29): 30375-84). It is generally believed that converting the monoclonal antibody to single chain antibody will not change the antigen binding epitope specificity. In order to further verify that the bifunctional antibody of the present invention can bind to the cryptic epitope, two recombinant proteins containing the epitope were taken as antigens for the ELISA assay in the present experiments.

Experimental procedures are as follows:

1) Protein coating: three antigens including rEGFRvIIIex (EGFRvIII extracellular domain protein, the preparation method of which was shown in patent WO/2011/035465), recombinant protein N12-CC16 (a fusion polypeptide composed of N1N2 domain from pIII protein of phage M13 and CC16, the preparation method of which was shown in Jiang H, et al., J Biol. Chem., 2011, 286 (7): 5913-20) and BSA (purchased from Shanghai Biological Engineering Co., Ltd.) control protein, were used to coat each well of 96-well plates with a dose of 50 ng per well (1 ng/µl, 50 µl/well) and incubated at 37° C. for 2 h.

2) Blocking: The plates were washed with 0.1M phosphate buffer (PBS) for 3 times, and the 5% PBS skim milk powder (Bright Dairy Co., Ltd) then was added and blocked at 37° C. for 2 h.

3) The antibodies 806/CD3, 7B3/CD3 to be tested were diluted into 2 ng/µL using 5% PBS skim milk powder at 50 µL/well and incubated at 37° C. for 1 h.

4) After three times of washing with PBST (PBS+0.05% Tween20), anti-6xHis-mouse monoclonal antibody (purchased from Shanghai Genomics, Inc) diluted at 1:1000 to 50 µl/well was added and incubated at 37° C. for 1 h.

5) After 3 times of washing with PBST, goat anti-mouse IgG-HRP (purchased from Santa Cruz Inc.) diluted at 1:2000 was added and then incubated at 37° C. for 1 h.

6) Coloration: The plates were washed with PBST for 5 times. ABTS color liquid was then added by 100 µL/well and the plates were colored at 37° C. in the dark for 10 min.

7) Detection: Bio-Rad Model 680 Microplate Reader was used to detect the absorbance at a wavelength of 405 nm.

Results

As shown in FIGS. 5A-5B: the bifunctional antibodies 806/CD3 and 7B3/CD3 can specifically bind to N12-CC16 (CC16 is fuse-expressed at the carboxyl terminal of N1N2 domain from pIII protein of M13 phage) and rEGFRvIIIex respectively. The binding strength of these two antibodies to the above-mentioned two antigens was significantly different from their nonspecific binding to BSA.

Since the common EGFR amino acid sequence in these two antigens is only CC16 polypeptide sequence, thus the binding epitopes of the bifunctional antibodies 806/CD3 and 7B3/CD3 are both CC16 polypeptide, namely ($^{287}$CKGYEDSRVMEAGDEC$^{302}$).

Example 6

Biological Activity Analysis of the Single Chain Bifunctional Antibodies 806/CD3 and 7B3/CD3—Cytotoxicities on Various Cancer Cells Peripheral blood mononuclear cells (PBMC) was isolated from the blood of healthy human donor with Ficoll (from Biochrom) density gradient centrifugation according to the standard procedures. After centrifugation, the cells were washed with 0.1M of phosphate buffer solutions (PBS) and resuspended in complete medium (RPMI 1640, Gibco). The cell density was adjusted to $5\times10^5$/mL. PBMC was used as effector cells in the cytotoxicity experiment. Different tumor cells were used as target cells. The density of the target cells was adjusted to $5\times10^4$/mL using RPMI 1640 complete medium. Target cells and effector cells of same volume were mixed to obtain an effector cell:target cell (E:T) ratio of 10:1.

The mixed cell suspension was added into the 96-well plate at a volume of 75 µL/well. 25 µL of a series of ten times gradient dilution of the following reagents (the concentrations are from 1000 ng/mL to 0.1 ng/mL) were added into each well:
1) 7B3/CD3 single chain bifunctional antibody
2) 806/CD3 single chain bifunctional antibody
3) RPMI 1640 complete medium (background control)
4) NGR/CD3 single chain bifunctional antibody (negative control, NGR is a peptide targeting new vessels without cross binding site to EGFR. It was prepared according to conventional methods)

After incubation in a incubator with 5% $CO_2$ at 37° C. for 40 hours, the cytotoxicity effects of the antibodies were detected with CytoTox96® Non-Radioactive Cytotoxicity Assay kit (from Promega) according to the manufacturer's instructions.

CytoTox 96® non-radioactive cytotoxicity assay is based on colorimetric method, which can replace the $^{51}$Cr release assay. CytoTox 96® assay can measure lactate dehydrogenase (LDH) quantitatively. LDH, a stable cytoplasmic enzyme, will be released in cell lysis. The way it releases is basically the same with the release of $^{51}$Cr in radioactive assay. The release of LDH in supernatant of culture medium can be detected by coupled enzymatic reaction in 30 minutes. During enzymatic reaction, LDH can transform tetrazolium (INT) into red formazan. The number of lysed cells was proportional to the amount of the red product.

The six types of EGFR-related cancer cells listed in the following table 1 were used to analyze the cancer cell killing capacity of the T cells mediated by the two bifunctional antibodies 7B3/CD3 and 806/CD3 of the present invention as well as EGFR-unrelated NGR/CD3 single chain bifunctional antibody as negative control.

Cancer cell killing ratio (i.e., cytotoxicity %) is calculated based on the following formula provided by the instruction manual of CytoTox96® non-radioactive cytotoxicity assay G1780:

$$\text{cytotoxicity \%} = \frac{\text{Experimental} - \text{Effector Spontaneous} - \text{Target Spontaneous}}{\text{Target Maximum} - \text{Target Spontaneous}} \times 100$$

wherein:

"Experimental" refers to the LDH release value generated in the experimental well added with antibody/effector cell/target cells, "Effector Spontaneous" refers to the LDH release spontaneously generated by effector cells, "Target Spontaneous" refers to the LDH release generated by cells without treatment of other factors, "Target Maximum" refers to the LDH release generated after the complete lysis of the target cells treated with 0.8% Triton X-100, "Target Maximum-Target Spontaneous" represents the LDH release generated in the complete lysis of the target cells treated with external factors.

TABLE 1

| Cancer cell lines | Characteristics | Cytotoxicity % of 1000 ng/ml of antibody 7B3/CD3 | Cytotoxicity % of 1000 ng/ml of antibody 806/CD3 | Cytotoxicity % 1000 ng/ml of antibody NGR/CD3 |
|---|---|---|---|---|
| U87 MG | Low level expression of endogenous EGFR | 1.3 | 9.4 | 3.49 |
| U87 MG-EGFRvIII, | U87 MG cells expressing EGFR with deletion of exons 2-7 | 72.6 | 97.9 | 10.5 |
| U87 MG-de4 EGFR | U87 MG cells expressing EGFR with deletion of exon 4 | 23.3 | 28.7 | 8.33 |
| A431 | Overexpressing endogenous EGFR | 47.2 | 55.2 | 6.09 |
| NCI-H1975 | EGFR with L85R/T790M mtuation | 75.2 | 50 | 11.5 |

TABLE 1-continued

| Cancer cell lines | Characteristics | Cytotoxicity % of 1000 ng/ml of antibody 7B3/CD3 | Cytotoxicity % of 1000 ng/ml of antibody 806/CD3 | Cytotoxicity % 1000 ng/ml of antibody NGR/CD3 |
|---|---|---|---|---|
| NCI-H1650 | exon 19 of EGFR with the deletion of 19E746-A750 | 52 | 69.4 | 3.05 |

The results shown in Table 1 indicates that cancer cells expressing EGFR mutants or overexpressing EGFR such as A431, U87 MG-de4 EGFR etc. would be killed specifically by T cells guided by bifunctional specific antibodies 7B3/CD3 or 806/CD3.

Specifically, the minimal specific cytotoxicity % is 23.3 while the maximal specific cytotoxicity % is 75.2 in the above-mentioned cancer cell groups treated with 7B3/CD3; the minimal specific cytotoxicity % is 28.7 while the maximal specific cytotoxicity % is 97.9 in the above-mentioned cancer cell groups treated with 806/CD3.

However, the cytotoxicity % of the above bifunctional specific antibodies 7B3/CD3 or 806/CD3 on cancer cells expressing low levels of endogenous normal EGFR (for instance, U87 MG) are very low (1.3 and 9.4 respectively), which are significantly lower than the cytotoxicity % on cancer cells expressing EGFR mutants or overexpressing EGFR.

More specifically, the cytotoxicity % of 7B3/CD3, 806/CD3 and the control antibody NGR/CD3 in different concentrations on various cancer cells are shown in the following tables 2-7.

TABLE 2

| | U87 MG | | |
|---|---|---|---|
| ng/ml | NGR/CD3 | 7B3/CD3 | 806/CD3 |
| 1000 | 3.49 ± 1.59 | 1.33 ± 2.00 | 9.42 ± 6.45 |
| 100 | 4.78 ± 1.61 | 1.16 ± 4.82 | 9.33 ± 4.37 |
| 10 | 5.63 ± 3.15 | 1.85 ± 3.18 | 8.95 ± 1.50 |
| 1 | 5.16 ± 3.41 | 0.04 ± 1.02 | 4.03 ± 1.44 |
| 0.1 | 5.47 ± 2.45 | 0.04 ± 1.26 | 5.12 ± 3.79 |

TABLE 3

| | U87 MG-EGFRvIII | | |
|---|---|---|---|
| ng/ml | NGR/CD3 | 7B3/CD3 | 806/CD3 |
| 1000 | 10.51 ± 2.47 | 72.64 ± 3.09 | 97.90 ± 4.18 |
| 100 | 4.95 ± 1.41 | 64.36 ± 1.64 | 92.98 ± 3.67 |
| 10 | 3.74 ± 2.79 | 58.29 ± 3.92 | 89.36 ± 1.28 |
| 1 | 3.19 ± 2.39 | 46.93 ± 2.76 | 66.30 ± 8.24 |
| 0.1 | 0.91 ± 1.07 | 6.17 ± 3.22 | 36.07 ± 6.77 |

TABLE 4

| | U87 MG-de4 EGFR | | |
|---|---|---|---|
| ng/ml | NGR/CD3 | 7B3/CD3 | 806/CD3 |
| 1000 | 8.33 ± 1.34 | 23.33 ± 2.68 | 28.69 ± 7.22 |
| 100 | 9.49 ± 2.23 | 19.51 ± 4.58 | 31.09 ± 1.57 |
| 10 | 6.05 ± 0.94 | 13.09 ± 5.15 | 18.43 ± 3.33 |

TABLE 4-continued

| | U87 MG-de4 EGFR | | |
|---|---|---|---|
| ng/ml | NGR/CD3 | 7B3/CD3 | 806/CD3 |
| 1 | 10.07 ± 4.14 | 5.60 ± 2.93 | 10.18 ± 2.87 |
| 0.1 | 7.66 ± 0.74 | 10.57 ± 2.05 | 5.16 ± 3.01 |

TABLE 5

| | A431 | | |
|---|---|---|---|
| ng/ml | NGR/CD3 | 7B3/CD3 | 806/CD3 |
| 1000 | 6.09 ± 3.19 | 47.23 ± 2.23 | 55.19 ± 2.15 |
| 100 | 5.26 ± 3.07 | 45.70 ± 1.65 | 48.77 ± 5.11 |
| 10 | 4.76 ± 2.94 | 38.73 ± 2.93 | 40.38 ± 5.16 |
| 1 | 0.20 ± 1.41 | 36.79 ± 2.44 | 34.71 ± 4.75 |
| 0.1 | 1.60 ± 0.91 | 13.03 ± 3.11 | 10.87 ± 1.09 |

TABLE 6

| | NCI-H1975 | | |
|---|---|---|---|
| ng/ml | NGR/CD3 | 7B3/CD3 | 806/CD3 |
| 1000 | 11.57 ± 5.32 | 75.22 ± 4.51 | 49.62 ± 0.76 |
| 100 | 9.41 ± 4.88 | 70.26 ± 5.72 | 35.87 ± 1.55 |
| 10 | 8.54 ± 4.78 | 41.67 ± 1.05 | 15.37 ± 3.51 |
| 1 | 7.15 ± 3.88 | 6.67 ± 1.22 | 5.48 ± 4.97 |
| 0.1 | 7.33 ± 3.79 | 1.10 ± 1.27 | 4.35 ± 3.53 |

TABLE 7

| | NCI-H1650 | | |
|---|---|---|---|
| ng/ml | NGR/CD3 | 7B3/CD3 | 806/CD3 |
| 1000 | 3.05 ± 0.72 | 51.97 ± 4.84 | 69.43 ± 7.97 |
| 100 | 5.90 ± 2.57 | 43.25 ± 9.84 | 61.86 ± 3.89 |
| 10 | 3.66 ± 0.63 | 35.60 ± 6.59 | 48.10 ± 1.63 |
| 1 | 4.95 ± 1.09 | 16.38 ± 2.99 | 20.67 ± 4.27 |
| 0.1 | 3.27 ± 2.49 | 9.13 ± 1.96 | 4.26 ± 1.98 |

Based on the cytotoxicity % and the concentration of the bifunctional antibodies shown in Tables 2-7 and FIGS. 6A-6F, the $EC_{50}$ value (concentration for 50% of maximal effect) of each bifunctional antibody against the tumor cells were calculated using GraphPad Prism 5 software (GraphPad Software Inc., San Diego, USA).

For example, as for U87 MG-EGFRvIII cells, the EC50 value of 7B3/CD3 single chain bifunctional antibody is 2.15 ng/ml while the EC50 value of 806/CD3 single chain bifunctional antibody is 0.29 ng/ml.

As for NCI-H1975 cells, the EC50 value of 7B3/CD3 single chain bifunctional antibody is 53.6 ng/ml while the EC50 value of 806/CD3 single chain bifunctional antibody is 1000 ng/ml.

The above low EC50 values of the bifuncitional antibodies in the present invention against the various cancer cell lines indicate that they have significant increased antitumor biological activities.

Example 7

In Vivo Antitumor Activities of the Bifunctional Antibody in Mice Bearing Tumor Xenografts 6- to 10-week old immunodeficient NOD/SCID mice (SHANGHAI SLAC LABORATORY ANIMAL CO. LTD) were used to establish human EGFR-related tumor xenograft models. The genetic characteristics of the mice are absence of functional T cells, B cells, NK cells as well as macrophages.

For the treatment group (n=6), the mixed cell suspension was subcutaneously inoculated in the right side of the mice. The cell suspension was composed of U87 MG-EGFRvIII or NCI-H1975 cancer cells at a cell concentration of $1 \times 10^6$/mL and unstimulated PBMC at a cell concentration of $1 \times 10^6$/mL with a volume ratio equal to 1:1.

After 1 hour of the inoculation of U87 MG-EGFRvIII/PBMC, mice were intravenously administered with 0.4 mg/kg/d and 0.04 mg/kg/d of 7B3/CD3 or 0.04 mg/kg of 806/CD3. The administration was repeated for 5 consecutive days.

After 1 hour of the inoculation of NCI-H1975/PBMC, mice were intravenously administered with 0.4 mg/kg/d and 0.04 mg/kg/d of 7B3/CD3. The administration was repeated for 10 consecutive days.

The control groups include two PBS vehicle administration groups (control group 1 is the group injected with tumor cells alone while the control group 2 is the group injected with tumor cells and PBMC) in order to evaluate the nonspecific cytotoxic effects induced by effector cells of PBMC.

In the specified day, caliper was used to measure the tumor size. The tumor volume was calculated according to the following formula:

$$\text{tumor volume} = \frac{\text{length} \times \text{width} \times \text{width}}{2}$$

The reduction of the tumor volume in the mouse models was set as the basis of the tumor inhibition effect of each single chain bifunctional antibody. The tumor inhibition rate in the following table was calculated according to the following formula:

$$\text{tumor inhibition rate} = 1 - \frac{\text{tumor volume of treatment group}}{\text{tumor volume of control group 2}} \times 100\%$$

TABLE 7

| Treatment group | Inhibition rate against U87 MG-EGFRvIII | Inhibition rate against NCI-H1975 |
|---|---|---|
| 806/CD3 | | |
| 0.4 mg/kg/d | — | — |
| 0.04 mg/kg/d | 74% | — |

TABLE 7-continued

| Treatment group | Inhibition rate against U87 MG-EGFRvIII | Inhibition rate against NCI-H1975 |
|---|---|---|
| 7B3/CD3 | | |
| 0.4 mg/kg/d | 80% | 87% |
| 0.04 mg/kg/d | 35.3% | 35% |

As shown in FIG. 7, in the mouse models bearing the U87 MG-EGFRvIII tumor cells, no obvious intervention on the U87 MG-EGFRvIII tumor growth in the mice of control group 2 (i.e. only injection of PBMC and tumor cells without bispecific antibody) as compared with the control group 1 (i.e. only injection of tumor cells) was observed.

However, antibodies 806/CD3 at a concentration of 0.04 mg/kg/d and 7B3/CD3 at a concentration of 0.4 mg/kg/d showed strong inhibition capacity on the growth of U87 MG-EGFRvIII. On 23 day after cell inoculation, their inhibition rates were 74% and 80% respectively (compared with the control group 2, p<0.05). In the lower dose of 7B3/CD3 (0.04 mg/kg/d), tumor growth inhibition rate was 35.3% (compared with the control group 2).

As shown in FIG. 8, in the mice model bearing NCI-1975 tumor cells, somewhat intervention effect on NCI-1975 tumor growth can be observed when comparing the group 2 with the group 1. However, the effect is less than that of the mice treated with 7B3/CD3 at a dose of 0.04 mg/kg/d, and significantly less than that of the mice treated with 7B3/CD3 at a dose of 0.4 mg/kg/d.

When compared with control groups 1 and 2, 7B3/CD3 treated mice display a dose-dependent antitumor growth effect. 1 of the 6 mice administered with 0.4 mg/kg/d antibody had no tumor outgrowth on the day 30 after the cell inoculation while all the mice administered with 0.04 mg/kg/d antibody had tumor outgrowth. When compared with control group 2, the tumor inhibition rates of these two groups are 87% (p<0.05) for the group of 0.4 mg/kg/d, and 35% (p<0.05) for the group of 0.04 mg/kg/d respectively.

Example 8

Biological Activity Analysis of the Single Chain Bifunctional Antibody 806/CD3 of the Present Invention and Humanized Monoclonal Antibody CH806—Cytotoxicities on Various Cancer Cells Two experimental groups were included in this assay, i.e. the three types of cancer cells treated with 806/CD3 and the three types of cancer cells treated with ch806. The preparations of the materials used in this assay are substantially the same with those in Example 6 except for: (1) the humanized monoclonal antibody ch806, the preparation method of which is as follows: the nucleotide sequences encoding the heavy chain and light chain variable regions of ch806 was synthesized according to the sequence disclosed in CN 102405235A. NheI and ApaI restriction enzyme cutting sites were introduced into the two terminals of the heavy chain encoding sequence while the EcoRV and BsiwI restriction enzyme cutting sites were introduced into the two terminals of the light chain encoding sequence. Next, by referring to for example CN101602808B and especially Example 7, the above heavy chain variable region and light chain variable region were loaded into expression vectors pH and pK respectively to obtain pH-ch806 and pK-ch806. The pH-ch806 and pK-ch806 were then co-transfected into CHO-DG44 cells (Invitrogen) according to the liposome transfection method. After MTX screening, the positive clones with high level antibody expressions were picked out. The cells were acclimated at the same time to adapt to the serum-free medium. The CHO-ch806 cells obtained by successful acclimation were cultured in serum-free medium and the serum-free cultured supernatant was collected for affinity purification with protein A (Code No. 17-5280-02, GE Healthcare Life Science) to obtain the purified protein of antibody ch806. (2) U87 MG EGFR cell, which is U87 MG cell line overexpressing EGFR, its construction method may refer to the reference (Wang H, Neoplasia, 2011, 13(5): 461-471), U87 MG can be available from ATCC.

The mixed tumor cell suspension prepared according to the description in the first and second paragraphs of Example 6 was added into the 96-well plates at a volume of 75 μL per well. Then 25 μL of 10 fold dilution (the concentrations range from 20 nM to 0.0002 nM) of the following reagents were added into each well respectively: bifunctional antibody 806/CDE and humanized antibody ch806.

The method and procedures for the cytotoxicity assay of the above-mentioned antibodies against the tumor cells are the same with those described in Example 6. The following Tables 8-10 record the cytotoxicity percentages of the bifunctional antibody 806/CD3 and humanized antibody ch806 against three different tumor cell lines.

TABLE 8

| nM | U87 MG | |
|---|---|---|
| | 806/CD3 | ch806 |
| 20 | 10.52 ± 0.83 | 4.18 ± 0.72 |
| 2 | 9.25 ± 1.87 | 0.28 ± 1.28 |
| 0.2 | 6.72 ± 2.52 | 0.07 ± 1.05 |
| 0.02 | 4.52 ± 2.92 | 0.71 ± 0.56 |
| 0.002 | 1.34 ± 2.80 | 0.71 ± 0.72 |
| 0.0002 | 0.75 ± 1.23 | 0.96 ± 0.91 |

TABLE 9

| nM | U87 MG EGFR | |
|---|---|---|
| | 806/CD3 | ch806 |
| 20 | 47.91 ± 5.54 | 4.92 ± 1.24 |
| 2 | 43.30 ± 3.51 | 0.49 ± 0.53 |
| 0.2 | 18.05 ± 5.05 | 0.37 ± 0.34 |
| 0.02 | 2.94 ± 5.70 | 1.31 ± 1.35 |
| 0.002 | 1.98 ± 3.59 | 0.61 ± 1.37 |
| 0.0002 | 0.60 ± 2.60 | 1.89 ± 1.22 |

TABLE 10

| nM | U87 MG EGFRvIII | |
|---|---|---|
| | 806/CD3 | ch806 |
| 20 | 88.70 ± 2.40 | 36.32 ± 3.83 |
| 2 | 82.42 ± 1.09 | 22.33 ± 2.85 |
| 0.2 | 63.66 ± 0.69 | 15.55 ± 3.26 |
| 0.02 | 36.45 ± 0.37 | 0.76 ± 2.69 |
| 0.002 | 9.50 ± 0.13 | 0.62 ± 0.58 |
| 0.0002 | 2.36 ± 0.54 | 0.41 ± 0.19 |

Based on the cytotoxicity % and the concentrations of the used antibodies in the above Tables 8-10 and FIGS. 9A-9C, the $EC_{50}$ values of the bifunctional antibody and the monoclonal antibody against the cancer cells were calculated by GraphPad Prism 5 software (GraphPad Software Inc., San Diego, USA).

As for U87 MG-EGFRvIII cells, $EC_{50}$ values of the single chain bifunctional antibody 806/CD3 is 0.136 nM, while $EC_{50}$ values of monoclonal antibody ch806 is 40.79 nM. As for MG-EGFR cells, $EC_{50}$ values of the single chain bifunctional antibody 806/CD3 is 23.43 nM, while $EC_{50}$ values of monoclonal antibody ch806 is 6476.08 nM. These results indicate that the single chain bifunctional antibody 806/CD3 of the present invention has a significantly increased cytotoxicity against tumor cells when compared with the humanized monoclonal antibody ch806.

TABLE 11

Description of the amino acids and nucleotides sequences of the present invention:

| | |
|---|---|
| SEQ ID NO: 1 | $EGFR_{287-302}$ cryptic epitope amino acid sequence |
| SEQ ID NO: 2 | 7B3 VH CDR1 amino acid sequence |
| SEQ ID NO: 3 | 7B3 VH CDR2 amino acid sequence |
| SEQ ID NO: 4 | 7B3 VH CDR3 amino acid sequence |
| SEQ ID NO: 5 | 7B3 VL CDR1 amino acid sequence |
| SEQ ID NO: 6 | 7B3 VL CDR2 amino acid sequence |
| SEQ ID NO: 7 | 7B3 VL CDR3 amino acid sequence |
| SEQ ID NO: 8 | 806/CD3 single chain bifuntional antibody amino acid sequence, i.e. $[V_{L806}\text{-linker-}V_{H806}\text{-linker-}V_{HCD3}\text{-linkder-}V_{LCD3}]$ |
| SEQ ID NO: 9 | 7B3/CD3 single chain bifuntional antibody amino acid sequence, i.e. $[V_{L7B3}\text{-linker-}V_{H7B3}\text{-linker-}V_{HCD3}\text{-linker-}V_{LCD3}]$ |
| SEQ ID NO: 10 | 806/CD3 single chain bifuntional antibody nucleotide sequence |
| SEQ ID NO: 11 | 7B3/CD3 single chain bifuntional antibody nucleotide sequence |
| SEQ ID NO: 12 | 7B3 single chain antibody nucleotide sequence $[V_{L7B3}\text{-linker-VH7B3-linker}]$ nucleotide sequence |
| SEQ ID NO: 13 | 7B3 VH nucleotide sequence |
| SEQ ID NO: 14 | 7B3 VL nucleotide sequence |
| SEQ ID NO: 15 | 5'L806-2 |
| SEQ ID NO: 16 | 3'L806 |
| SEQ ID NO: 17 | 5'H806-2 |
| SEQ ID NO: 18 | 3'H806 |
| SEQ ID NO: 19 | 5'L7B3-2 |
| SEQ ID NO: 20 | 5'L7B3-1 |
| SEQ ID NO: 21 | 3'L7B3 |
| SEQ ID NO: 22 | 5'H7B3 |
| SEQ ID NO: 23 | 3'H7B3 |
| SEQ ID NO: 24 | 5'HCD3 |
| SEQ ID NO: 25 | 3'HCD3 |
| SEQ ID NO: 26 | 5'LCD3 |
| SEQ ID NO: 27 | 3'LCD3 |
| SEQ ID NO: 28 | 5'H806-1 |
| SEQ ID NO: 29 | 3'H7B3-2 |

The invention claimed is:

1. A multi-functional antibody polypeptide, comprising:
   (a) a first functional domain that binds specifically to an epitope consisting of 287th to 302nd amino acids of EGFR, shown as SEQ ID NO. 1, wherein the first functional domain comprises an antibody heavy chain variable region comprising SEQ ID NOs: 2, 3, and 4, and an antibody light chain variable region comprising SEQ ID NOs: 5, 6, and 7; and
   (b) a second functional domain that binds specifically to a surface antigen of a human T cell.

2. The polypeptide of claim 1, wherein the second functional domain is a single chain anti-CD3 antibody.

3. The polypeptide of claim 1, further comprising a linker located between the first and the second functional domains or located between complementarity determining regions inside the first or the second functional domain.

4. The polypeptide of claim 3, wherein the sequence of the linker is (GlyGlyGlyGlySer)n, where n is an integer from 1 to 5.

5. The polypeptide of claim 4, wherein n=3.

6. The polypeptide of claim 1, wherein the first or the second functional domain is selected from intact antibody, single chain antibody (scFv), Fab fragment, Fd fragment, Fv fragment, F(ab')$_2$ fragment, and derivatives thereof.

7. The polypeptide of claim 1, wherein the first and/or the second functional domain is humanized, chimeric, or derived from a mouse.

8. The polypeptide of claim 1, having the amino acid sequence shown in SEQ ID NO. 9.

* * * * *

SEQUENCE LISTING

<160> NUMBER OF SEQ ID NOS: 29

<210> SEQ ID NO 1
<211> LENGTH: 16
<212> TYPE: PRT
<213> ORGANISM: homo sapiens

<400> SEQUENCE: 1

Cys Gly Ala Asp Ser Tyr Glu Met Glu Glu Asp Gly Val Arg Lys Cys
1               5                   10                  15

<210> SEQ ID NO 2
<211> LENGTH: 9
<212> TYPE: PRT
<213> ORGANISM: homo sapiens

<400> SEQUENCE: 2

Ser Ile Thr Ser Asp Tyr Ala Trp Asn
1               5

<210> SEQ ID NO 3
<211> LENGTH: 16
<212> TYPE: PRT
<213> ORGANISM: homo sapiens

<400> SEQUENCE: 3

Tyr Ile Ser Tyr Arg Gly Arg Thr Ser Tyr Asn Pro Ser Leu Lys Ser
1               5                   10                  15

<210> SEQ ID NO 4
<211> LENGTH: 7
<212> TYPE: PRT
<213> ORGANISM: homo sapiens

<400> SEQUENCE: 4

Leu Gly Arg Gly Phe Arg Tyr
1               5

<210> SEQ ID NO 5
<211> LENGTH: 11
<212> TYPE: PRT
<213> ORGANISM: homo sapiens

<400> SEQUENCE: 5

His Ala Ser Gln Asp Ile Asn Ser Asn Ile Gly
1               5                   10

<210> SEQ ID NO 6
<211> LENGTH: 7
<212> TYPE: PRT
<213> ORGANISM: homo sapiens

<400> SEQUENCE: 6

His Gly Lys Asn Leu Glu Asp
1               5

<210> SEQ ID NO 7
<211> LENGTH: 10
<212> TYPE: PRT
<213> ORGANISM: homo sapiens

<400> SEQUENCE: 7

Val Gln Tyr Ala Gln Phe Pro Tyr Thr Phe
1               5                   10

<210> SEQ ID NO 8
<211> LENGTH: 488
<212> TYPE: PRT
<213> ORGANISM: artificial sequence
<220> FEATURE:
<223> OTHER INFORMATION: Synthetic Polypeptide

<400> SEQUENCE: 8

```
Asp Ile Leu Met Thr Gln Ser Pro Ser Ser Met Ser Val Ser Leu Gly
1               5                   10                  15

Asp Thr Val Ser Ile Thr Cys His Ser Ser Gln Asp Ile Asn Ser Asn
            20                  25                  30

Ile Gly Trp Leu Gln Gln Arg Pro Gly Lys Ser Phe Lys Gly Leu Ile
        35                  40                  45

Tyr His Gly Thr Asn Leu Asp Asp Glu Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Trp
                85                  90                  95

Thr Phe Gly Gly Gly Thr Lys Leu Glu Ile Lys Arg Gly Gly Gly Gly
            100                 105                 110

Ser Gly Gly Gly Gly Ser Gly Gly Gly Ser Ala Asp Val Gln Leu
        115                 120                 125

Gln Glu Ser Gly Pro Ser Leu Val Lys Pro Ser Gln Ser Leu Ser Leu
130                 135                 140

Thr Cys Thr Val Thr Gly Tyr Ser Ile Thr Ser Asp Phe Ala Trp Asn
145                 150                 155                 160

Trp Ile Arg Gln Phe Pro Gly Asn Lys Leu Glu Trp Met Gly Tyr Ile
                165                 170                 175

Ser Tyr Ser Gly Asn Thr Arg Tyr Asn Pro Ser Leu Lys Ser Arg Ile
            180                 185                 190

Ser Ile Thr Arg Asp Thr Ser Lys Asn Gln Phe Phe Leu Gln Leu Asn
        195                 200                 205

Ser Val Thr Ile Glu Asp Thr Ala Thr Tyr Tyr Cys Val Thr Ala Gly
    210                 215                 220

Arg Gly Phe Pro Tyr Trp Gly Gln Gly Thr Leu Val Thr Val Ser Ala
225                 230                 235                 240

Gly Gly Gly Gly Ser Asp Ile Lys Leu Gln Gln Ser Gly Ala Glu Leu
                245                 250                 255

Ala Arg Pro Gly Ala Ser Val Lys Met Ser Cys Lys Thr Ser Gly Tyr
            260                 265                 270

Thr Phe Thr Arg Tyr Thr Met His Trp Val Lys Gln Arg Pro Gly Gln
        275                 280                 285

Gly Leu Glu Trp Ile Gly Tyr Ile Asn Pro Ser Arg Gly Tyr Thr Asn
    290                 295                 300

Tyr Asn Gln Lys Phe Lys Asp Lys Ala Thr Leu Thr Thr Asp Lys Ser
305                 310                 315                 320

Ser Ser Thr Ala Tyr Met Gln Leu Ser Ser Leu Thr Ser Glu Asp Ser
                325                 330                 335

Ala Val Tyr Tyr Cys Ala Arg Tyr Tyr Asp Asp His Tyr Cys Leu Asp
            340                 345                 350

Tyr Trp Gly Gln Gly Thr Thr Leu Thr Val Ser Ser Val Glu Gly Gly
        355                 360                 365
```

```
Ser Gly Gly Ser Gly Gly Ser Gly Gly Val Asp Asp Ile
    370             375             380

Gln Leu Thr Gln Ser Pro Ala Ile Met Ser Ala Ser Pro Gly Glu Lys
385                 390                 395                 400

Val Thr Met Thr Cys Arg Ala Ser Ser Val Ser Tyr Met Asn Trp
                405                 410                 415

Tyr Gln Gln Lys Ser Gly Thr Ser Pro Lys Arg Trp Ile Tyr Asp Thr
            420                 425                 430

Ser Lys Val Ala Ser Gly Val Pro Tyr Arg Phe Ser Gly Ser Gly Ser
        435                 440                 445

Gly Thr Ser Tyr Ser Leu Thr Ile Ser Ser Met Glu Ala Glu Asp Ala
    450                 455                 460

Ala Thr Tyr Tyr Cys Gln Gln Trp Ser Ser Asn Pro Leu Thr Phe Gly
465                 470                 475                 480

Ala Gly Thr Lys Leu Glu Leu Lys
                485

<210> SEQ ID NO 9
<211> LENGTH: 488
<212> TYPE: PRT
<213> ORGANISM: artificial sequence
<220> FEATURE:
<223> OTHER INFORMATION: Synthetic Polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Asn Ser Asn
            20                  25                  30

Ile Gly Trp Leu Gln Gln Lys Pro Gly Lys Ala Phe Lys Gly Leu Ile
        35                  40                  45

Tyr His Gly Lys Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Gln Tyr Ala Gln Phe Pro Tyr
                85                  90                  95

Thr Phe Gly Gln Gly Thr Lys Val Glu Ile Lys Arg Ser Gly Gly Gly
            100                 105                 110

Gly Ser Gly Gly Gly Gly Ser Gly Gly Gly Ser Asp Val Gln Leu
        115                 120                 125

Val Glu Ser Gly Gly Gly Leu Val Gln Pro Gly Gly Ser Leu Arg Leu
130                 135                 140

Ser Cys Ala Val Ser Gly Tyr Ser Ile Thr Ser Asp Tyr Ala Trp Asn
145                 150                 155                 160

Trp Ile Arg Gln Ala Pro Gly Lys Gly Leu Glu Trp Leu Gly Tyr Ile
                165                 170                 175

Ser Tyr Arg Gly Arg Thr Ser Tyr Asn Pro Ser Leu Lys Ser Arg Ile
            180                 185                 190

Ser Ile Thr Arg Asp Asn Ser Lys Asn Thr Phe Phe Leu Gln Leu Asn
        195                 200                 205

Ser Leu Arg Ala Glu Asp Thr Ala Val Tyr Tyr Cys Ala Arg Leu Gly
    210                 215                 220

Arg Gly Phe Arg Tyr Trp Gly Gln Gly Thr Leu Val Thr Val Ser Ser
225                 230                 235                 240
```

Gly Gly Gly Gly Ser Asp Ile Lys Leu Gln Gln Ser Gly Ala Glu Leu
            245                 250                 255

Ala Arg Pro Gly Ala Ser Val Lys Met Ser Cys Lys Thr Ser Gly Tyr
        260                 265                 270

Thr Phe Thr Arg Tyr Thr Met His Trp Val Lys Gln Arg Pro Gly Gln
    275                 280                 285

Gly Leu Glu Trp Ile Gly Tyr Ile Asn Pro Ser Arg Gly Tyr Thr Asn
290                 295                 300

Tyr Asn Gln Lys Phe Lys Asp Lys Ala Thr Leu Thr Thr Asp Lys Ser
305                 310                 315                 320

Ser Ser Thr Ala Tyr Met Gln Leu Ser Ser Leu Thr Ser Glu Asp Ser
                325                 330                 335

Ala Val Tyr Tyr Cys Ala Arg Tyr Tyr Asp Asp His Tyr Cys Leu Asp
            340                 345                 350

Tyr Trp Gly Gln Gly Thr Thr Leu Thr Val Ser Ser Val Glu Gly Gly
        355                 360                 365

Ser Gly Gly Ser Gly Gly Ser Gly Gly Ser Gly Gly Val Asp Asp Ile
    370                 375                 380

Gln Leu Thr Gln Ser Pro Ala Ile Met Ser Ala Ser Pro Gly Glu Lys
385                 390                 395                 400

Val Thr Met Thr Cys Arg Ala Ser Ser Ser Val Ser Tyr Met Asn Trp
                405                 410                 415

Tyr Gln Gln Lys Ser Gly Thr Ser Pro Lys Arg Trp Ile Tyr Asp Thr
            420                 425                 430

Ser Lys Val Ala Ser Gly Val Pro Tyr Arg Phe Ser Gly Ser Gly Ser
        435                 440                 445

Gly Thr Ser Tyr Ser Leu Thr Ile Ser Ser Met Glu Ala Glu Asp Ala
    450                 455                 460

Ala Thr Tyr Tyr Cys Gln Gln Trp Ser Ser Asn Pro Leu Thr Phe Gly
465                 470                 475                 480

Ala Gly Thr Lys Leu Glu Leu Lys
                485

<210> SEQ ID NO 10
<211> LENGTH: 1570
<212> TYPE: DNA
<213> ORGANISM: artificial sequence
<220> FEATURE:
<223> OTHER INFORMATION: Synthetic Polynucleotide
<220> FEATURE:
<221> NAME/KEY: misc_feature
<222> LOCATION: (4)..(9)
<223> OTHER INFORMATION: site for enzyme digestion

<400> SEQUENCE: 10

```
ctagctagcc accatggtgt ccacagctca gttccttgca ttcttgttgc tttggtttcc      60
aggtgcaaga tgtgacatcc tgatgaccca atctccatcc tccatgtctg tatctctggg     120
agacacagtc agcatcactt gccattcaag tcaggacatt aacagtaata tagggtggtt     180
gcagcagaga ccagggaaat catttaaggg cctgatctat catggaacca acttggacga     240
tgaagttcca tcaaggttca gtggcagtgg atctggagcc gattattctc tcaccatcag     300
cagcctggaa tctgaagatt ttgcagacta ttactgtgta cagtatgctc agtttccgtg     360
gacgttcggt ggaggcacca agctggaaat caaacgtggt ggaggcggtt caggcggagg     420
tggctctggc ggtggcggat cggccgatgt gcagcttcag gagtcgggac ctagcctggt     480
gaaaccttct cagtctctgt ccctcacctg cactgtcact ggctactcaa tcaccagtga     540
```

```
ttttgcctgg aactggatcc ggcagtttcc aggaaacaag ctggagtgga tgggctacat    600
aagttatagt ggtaacacta ggtacaaccc atctctcaaa agtcgaatct ctatcactcg    660
agacacatcc aagaaccaat tcttcctgca gttgaattct gtgactattg aggacacagc    720
cacatattac tgtgtaacgg cgggacgcgg gtttccttat tggggccaag ggactctggt    780
cactgtctct gcaggaggtg gtggatccga tatcaaactg cagcagtcag gggctgaact    840
ggcaagacct ggggcctcag tgaagatgtc ctgcaagact tctggctaca cctttactag    900
gtacacgatg cactgggtaa acagaggcc tggacagggt ctggaatgga ttggatacat    960
taatcctagc cgtggttata ctaattacaa tcagaagttc aaggacaagg ccacattgac   1020
tacagacaaa tcctccagca cagcctacat gcaactgagc agcctgacat ctgaggactc   1080
tgcagtctat tactgtgcaa gatattatga tgatcattac tgccttgact actggggcca   1140
aggcaccact ctcacagtct cctcagtcga aggtggaagt ggaggttctg gtggaagtgg   1200
aggttcaggt ggagtcgacg acattcagct gacccagtct ccagcaatca tgtctgcatc   1260
tccagggag aaggtcacca tgacctgcag agccagttca agtgtaagtt acatgaactg   1320
gtaccagcag aagtcaggca cctcccccaa aagatggatt tatgacacat ccaaagtggc   1380
ttctggagtc ccttatcgct tcagtggcag tgggtctggg acctcatact ctctcacaat   1440
cagcagcatg gaggctgaag atgctgccac ttattactgc caacagtgga gtagtaaccc   1500
gctcacgttc ggtgctggga ccaagctgga gctgaaacat catcaccatc atcattaggc   1560
ggccgcatag                                                         1570

<210> SEQ ID NO 11
<211> LENGTH: 1545
<212> TYPE: DNA
<213> ORGANISM: artificial sequence
<220> FEATURE:
<223> OTHER INFORMATION: Synthetic Polynucleotide

<400> SEQUENCE: 11
atggtgtcca cagctcagtt ccttgcattc ttgttgcttt ggtttccagg tgcaagatgt     60
gatattcaga tgacccagag cccgagcagc ctgagcgcga gcgtgggcga ccgtgtgacc    120
attacctgcc atgcgagcca ggatattaac agcaacattg ctggctgca gcagaaaccg    180
ggcaaagcgt ttaaggcct gatttatcat ggcaaaaacc tggaagatgg cgtgccgagc    240
cgttttagcg gcagcggcag cggcaccgat tttaccctga ccattagcag cctgcagccg    300
gaagattttg cgacctatta ttgcgttcag tacgcccagt tcccatatac atttggccag    360
ggcaccaaag tggaaattaa acgttcaggt ggaggcggtt caggcggagg tggctctggc    420
ggtggcggat cggatgtgca gctggtgaa gcggcggcg gcctggtgca gccgggcggc    480
agcctgcgtc tgagctgcgc ggtgagcggc tatagcatta ccagcgatta tgcgtggaac    540
tggattcgtc aggcgccggg caaaggcctg aatggctgg gctatattag ctatcgcggc    600
cgcaccagct ataacccgag cctgaaaagc cgtattagca ttaccgtga taacagcaaa    660
aacacctttt tcctgcagct gaacagcctg cgtgcggaag ataccgcggt gtattattgc    720
gcgcgcctgg gacgcggctt ccgctactgg ggccaggca ccctggtgac cgtgagcagc    780
ggaggtggtg gatccgatat caaactgcag cagtcagggg ctgaactggc aagacctggg    840
gcctcagtga agatgtcctg caagacttct ggctacacct ttactaggta cacgatgcac    900
tgggtaaaac agaggcctgg acagggtctg gaatggattg gatacattaa tcctagccgt    960
```

```
ggttatacta attacaatca gaagttcaag gacaaggcca cattgactac agacaaatcc   1020
tccagcacag cctacatgca actgagcagc ctgacatctg aggactctgc agtctattac   1080
tgtgcaagat attatgatga tcattactgc cttgactact ggggccaagg caccactctc   1140
acagtctcct cagtcgaagg tggaagtgga ggttctggtg aagtggagg ttcaggtgga   1200 gtcgacgaca ttcagctgac ccagtctcca gcaatcatgt ctgcatctcc aggggagaag   1260
gtcaccatga cctgcagagc cagttcaagt gtaagttaca tgaactggta ccagcagaag   1320
tcaggcacct cccccaaaag atggatttat gacacatcca aagtggcttc tggagtccct   1380
tatcgcttca gtggcagtgg gtctgggacc tcatactctc tcacaatcag cagcatggag   1440
gctgaagatg ctgccactta ttactgccaa cagtggagta gtaacccgct cacgttcggt   1500
gctgggacca agctggagct gaaacatcat caccatcatc attag                   1545

<210> SEQ ID NO 12
<211> LENGTH: 847
<212> TYPE: DNA
<213> ORGANISM: artificial sequence
<220> FEATURE:
<223> OTHER INFORMATION: Synthetic Polynucleotide

<400> SEQUENCE: 12
ctagctagcc accatggtgt ccacagctca gttccttgca ttcttgttgc tttggtttcc    60
aggtgcaaga tgtgatattc agatgaccca gagcccgagc agcctgagcg cgagcgtggg   120
cgaccgtgtg accattacct gccatgcgag ccaggatatt aacagcaaca ttggctggct   180
gcagcagaaa ccgggcaaag cgtttaaagg cctgatttat catggcaaaa acctggaaga   240
tggcgtgccg agccgtttta gcggcagcgg cagcggcacc gattttaccc tgaccattag   300
cagcctgcag ccggaagatt ttgcgaccta ttattgcgtt cagtacgccc agttcccata   360
tacatttggc cagggcacca aagtggaaat taaacgttca ggtggaggcg gttcaggcgg   420
aggtggctct ggcggtggcg gatcggatgt gcagctggtg gaaagcggcg gcggcctggt   480
gcagccgggc ggcagcctgc gtctgagctg cgcggtgagc ggctatagca ttaccagcga   540
ttatgcgtgg aactggattc gtcaggcgcc gggcaaaggc ctggaatggc tgggctatat   600
tagctatcgc ggccgcacca gctataaccc gagcctgaaa agccgtatta gcattacccg   660
tgataacagc aaaaacacct tttcctgca gctgaacagc ctgcgtgcgg aagataccgc   720
ggtgtattat tgcgcgcgcc tgggacgcgg cttccgctac tggggccagg gcaccctggt   780
gaccgtgagc agcggaggtg gtggatccga tatcaaactg cagcagtcag gggctgaact   840
ggcaaga                                                             847

<210> SEQ ID NO 13
<211> LENGTH: 348
<212> TYPE: DNA
<213> ORGANISM: artificial sequence
<220> FEATURE:
<223> OTHER INFORMATION: Synthetic Polynucleotide

<400> SEQUENCE: 13
gatgtgcagc tggtggaaag cggcggcggc ctggtgcagc cgggcggcag cctgcgtctg    60
agctgcgcgg tgagcggcta tagcattacc agcgattatg cgtggaactg gattcgtcag   120
gcgccgggca aaggcctgga atggctgggc tatattagct atcgcggccg caccagctat   180
aacccgagcc tgaaaagccg tattagcatt acccgtgata acagcaaaaa cacctttttc   240
ctgcagctga acagcctgcg tgcggaagat accgcggtgt attattgcgc gcgcctggga   300
```

```
cgcggcttcc gctactgggg ccagggcacc ctggtgaccg tgagcagc            348
```

<210> SEQ ID NO 14
<211> LENGTH: 324
<212> TYPE: DNA
<213> ORGANISM: artificial sequence
<220> FEATURE:
<223> OTHER INFORMATION: Synthetic Polynucleotide

<400> SEQUENCE: 14

```
gatattcaga tgacccagag cccgagcagc ctgagcgcga gcgtgggcga ccgtgtgacc    60
attacctgcc atgcgagcca ggatattaac agcaacattg gctggctgca gcagaaaccg   120
ggcaaagcgt ttaaaggcct gatttatcat ggcaaaaacc tggaagatgg cgtgccgagc   180
cgttttagcg gcagcggcag cggcaccgat tttaccctga ccattagcag cctgcagccg   240
gaagattttg cgacctatta ttgcgttcag tacgcccagt cccatatac atttggccag    300
ggcaccaaag tggaaattaa acgt                                          324
```

<210> SEQ ID NO 15
<211> LENGTH: 45
<212> TYPE: DNA
<213> ORGANISM: artificial sequence
<220> FEATURE:
<223> OTHER INFORMATION: Synthetic Polynucleotide

<400> SEQUENCE: 15

```
gttgctttgg tttccaggtg caagatgtga catcctgatg accca                    45
```

<210> SEQ ID NO 16
<211> LENGTH: 55
<212> TYPE: DNA
<213> ORGANISM: artificial sequence
<220> FEATURE:
<223> OTHER INFORMATION: Synthetic Polynucleotide

<400> SEQUENCE: 16

```
ccgccagagc cacctccgcc tgaaccgcct ccaccacgtt tgatttccag cttgg         55
```

<210> SEQ ID NO 17
<211> LENGTH: 49
<212> TYPE: DNA
<213> ORGANISM: artificial sequence
<220> FEATURE:
<223> OTHER INFORMATION: Synthetic Polynucleotide

<400> SEQUENCE: 17

```
gcggaggtgg ctctggcggt ggcggatcgg ccgatgtgca gcttcagga              49
```

<210> SEQ ID NO 18
<211> LENGTH: 30
<212> TYPE: DNA
<213> ORGANISM: artificial sequence
<220> FEATURE:
<223> OTHER INFORMATION: Synthetic Polynucleotide

<400> SEQUENCE: 18

```
ggatccacca cctcctgcag agacagtgac                                    30
```

<210> SEQ ID NO 19
<211> LENGTH: 43
<212> TYPE: DNA
<213> ORGANISM: artificial sequence
<220> FEATURE:

<223> OTHER INFORMATION: Synthetic Polynucleotide

<400> SEQUENCE: 19
gttgctttgg tttccaggtg caagatgtga tattcagatg acc         43

<210> SEQ ID NO 20
<211> LENGTH: 59
<212> TYPE: DNA
<213> ORGANISM: artificial sequence
<220> FEATURE:
<223> OTHER INFORMATION: Synthetic Polynucleotide

<400> SEQUENCE: 20
ctagctagcc accatggtgt ccacagctca gttccttgca ttcttgttgc tttggtttc    59

<210> SEQ ID NO 21
<211> LENGTH: 42
<212> TYPE: DNA
<213> ORGANISM: artificial sequence
<220> FEATURE:
<223> OTHER INFORMATION: Synthetic Polynucleotide

<400> SEQUENCE: 21
acctccgcct gaaccgcctc cacctgaacg tttaatttcc ac          42

<210> SEQ ID NO 22
<211> LENGTH: 46
<212> TYPE: DNA
<213> ORGANISM: artificial sequence
<220> FEATURE:
<223> OTHER INFORMATION: Synthetic Polynucleotide

<400> SEQUENCE: 22
ttcaggcgga ggtggctctg gcggtggcgg atcggatgtg cagctg      46

<210> SEQ ID NO 23
<211> LENGTH: 27
<212> TYPE: DNA
<213> ORGANISM: artificial sequence
<220> FEATURE:
<223> OTHER INFORMATION: Synthetic Polynucleotide

<400> SEQUENCE: 23
ggatccacca cctccgctgc tcacggt                           27

<210> SEQ ID NO 24
<211> LENGTH: 31
<212> TYPE: DNA
<213> ORGANISM: artificial sequence
<220> FEATURE:
<223> OTHER INFORMATION: Synthetic Polynucleotide

<400> SEQUENCE: 24
ggaggtggtg gatccgatat caaactgcag c                      31

<210> SEQ ID NO 25
<211> LENGTH: 49
<212> TYPE: DNA
<213> ORGANISM: artificial sequence
<220> FEATURE:
<223> OTHER INFORMATION: Synthetic Polynucleotide

<400> SEQUENCE: 25
cacttccacc agaacctcca cttccacctt cgactgagga gactgtgag   49

```
<210> SEQ ID NO 26
<211> LENGTH: 42
<212> TYPE: DNA
<213> ORGANISM: artificial sequence
<220> FEATURE:
<223> OTHER INFORMATION: Synthetic Polynucleotide

<400> SEQUENCE: 26
ctggtggaag tggaggttca ggtggagtcg acgacattca gc                      42

<210> SEQ ID NO 27
<211> LENGTH: 44
<212> TYPE: DNA
<213> ORGANISM: artificial sequence
<220> FEATURE:
<223> OTHER INFORMATION: Synthetic Polynucleotide

<400> SEQUENCE: 27
ctatgcggcc gcctaatgat gatggtgatg atgtttcagc tcca                    44

<210> SEQ ID NO 28
<211> LENGTH: 59
<212> TYPE: DNA
<213> ORGANISM: artificial sequence
<220> FEATURE:
<223> OTHER INFORMATION: Synthetic Polynucleotide

<400> SEQUENCE: 28
ctagctagcc accatggtgt ccacagctca gttccttgca ttcttgttgc tttggtttc    59

<210> SEQ ID NO 29
<211> LENGTH: 55
<212> TYPE: DNA
<213> ORGANISM: artificial sequence
<220> FEATURE:
<223> OTHER INFORMATION: Synthetic Polynucleotide

<400> SEQUENCE: 29
tcttgccagt tcagccctg actgctgcag tttgatatcg gatccaccac ctccg         55
```